United States Patent
Shimoda et al.

(10) Patent No.: US 9,655,550 B2
(45) Date of Patent: May 23, 2017

(54) LATENT FINGERPRINT DETECTION METHOD, HEATING EVAPORATION DEVICE FOR DETECTING LATENT FINGERPRINT, LATENT FINGERPRINT DETECTION APPARATUS, AND COMPOSITION FOR DETECTING LATENT FINGERPRINT

(71) Applicants: EARTH CHEMICAL CO. LTD., Tokyo (JP); TOAGOSEI CO., LTD., Tokyo (JP)

(72) Inventors: Osamu Shimoda, Hyogo (JP); Yushi Sawada, Kobe (JP); Masao Fukushima, Hyogo (JP); Makoto Miyamoto, Aioi (JP); Yushi Ando, Nagoya (JP); Yuji Ishikawa, Osaka (JP)

(73) Assignees: EARTH CHEMICAL CO., LTD., Tokyo (JP); TOAGOSEI CO., LTD., Tokyo (JP)

(*) Notice: Subject to any disclaimer, the term of this patent is extended or adjusted under 35 U.S.C. 154(b) by 11 days.

(21) Appl. No.: 14/438,567

(22) PCT Filed: Oct. 11, 2013

(86) PCT No.: PCT/JP2013/077846
§ 371 (c)(1),
(2) Date: Apr. 24, 2015

(87) PCT Pub. No.: WO2014/065142
PCT Pub. Date: May 1, 2014

(65) Prior Publication Data
US 2015/0245790 A1    Sep. 3, 2015

(30) Foreign Application Priority Data

Oct. 25, 2012  (JP) .................. 2012-235678
Oct. 25, 2012  (JP) .................. 2012-236004

(51) Int. Cl.
*A61B 5/1172*    (2016.01)
*B05B 7/16*    (2006.01)
(Continued)

(52) U.S. Cl.
CPC .......... *A61B 5/1172* (2013.01); *B05B 7/1686* (2013.01); *B05B 15/12* (2013.01); *F24J 1/00* (2013.01); *A61B 5/0071* (2013.01)

(58) Field of Classification Search
CPC ..................................................... A61B 5/117
(Continued)

(56) References Cited

U.S. PATENT DOCUMENTS

2007/0026130 A1* 2/2007 Arndt .................. B41M 3/001
427/1
2010/0047433 A1    2/2010 Shimoda et al.

FOREIGN PATENT DOCUMENTS

JP    2-268744 A    11/1990
JP    11-9575 A    1/1999
(Continued)

OTHER PUBLICATIONS

International Search Report, PCT/JP2013/077846, Dec. 3, 2013, 1 pg.

*Primary Examiner* — Dah-Wei D Yuan
*Assistant Examiner* — Andrew Bowman
(74) *Attorney, Agent, or Firm* — Volpe and Koenig, P.C.

(57) ABSTRACT

The present invention provides a latent fingerprint detection method that is easy to handle and is capable of clearly detecting a latent fingerprint and a heating evaporation device for detecting a latent fingerprint and a latent fingerprint detection apparatus which are capable of detecting a clear latent fingerprint by a one-time operation by heating a chemical agent at high temperatures in a short time, as well as a composition for detecting a latent fingerprint. This latent (Continued)

fingerprint detection method includes a heating step of heating a chemical agent to be gasified by heating so as to attach to a latent fingerprint on a specimen, and an exposure step of exposing the specimen having the latent fingerprint attached thereto to the atmosphere of the gasified chemical agent. The chemical agent is a mixture of a 2-cyanoacrylic acid ester polymer and a dye.

7 Claims, 13 Drawing Sheets

(51) Int. Cl.
  *B05B 15/12* (2006.01)
  *F24J 1/00* (2006.01)
  *A61B 5/00* (2006.01)
(58) Field of Classification Search
  USPC .............................................................. 427/1
  See application file for complete search history.

(56) References Cited

FOREIGN PATENT DOCUMENTS

| | | | |
|---|---|---|---|
| JP | 2009-56110 A | 3/2009 | |
| JP | 2009-056110 A * | 12/2009 | ........... A61B 5/1172 |
| WO | 2008/044494 A1 | 4/2008 | |

\* cited by examiner

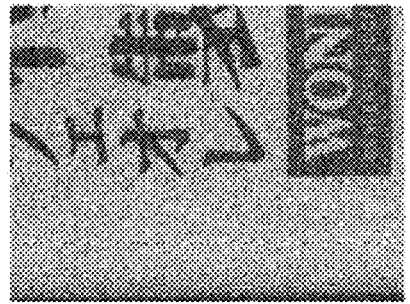
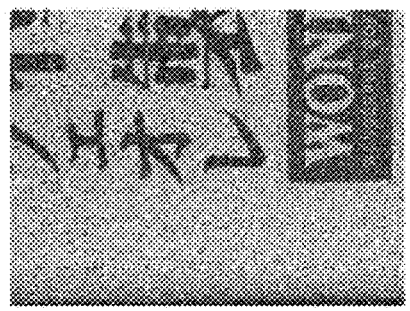
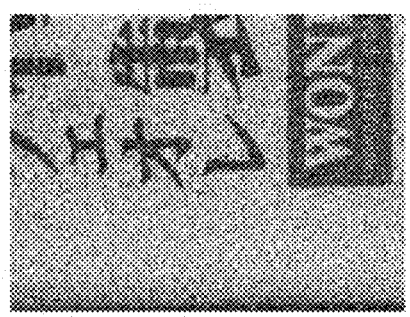
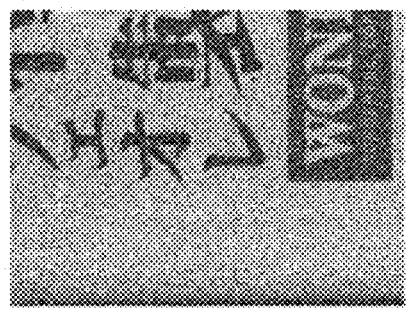

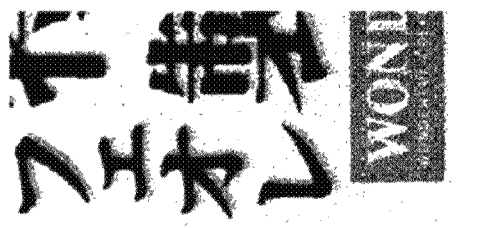
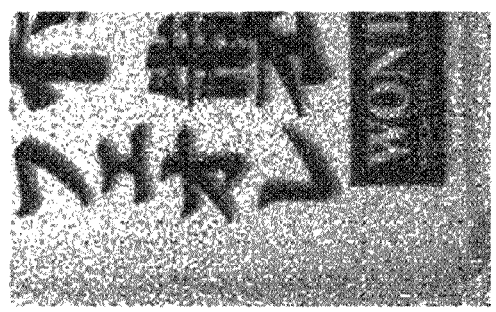
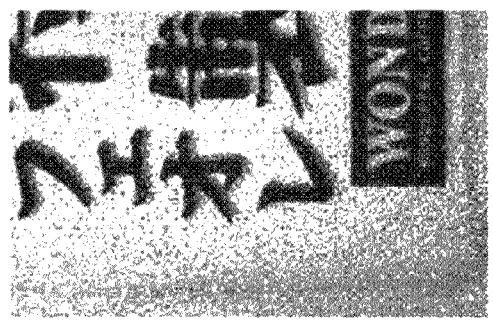
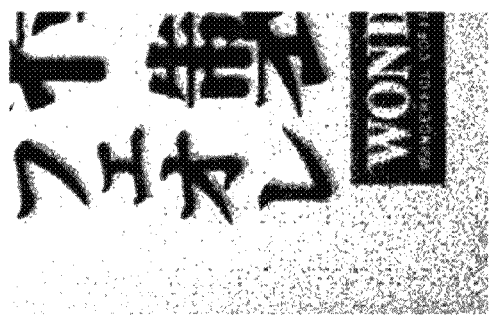

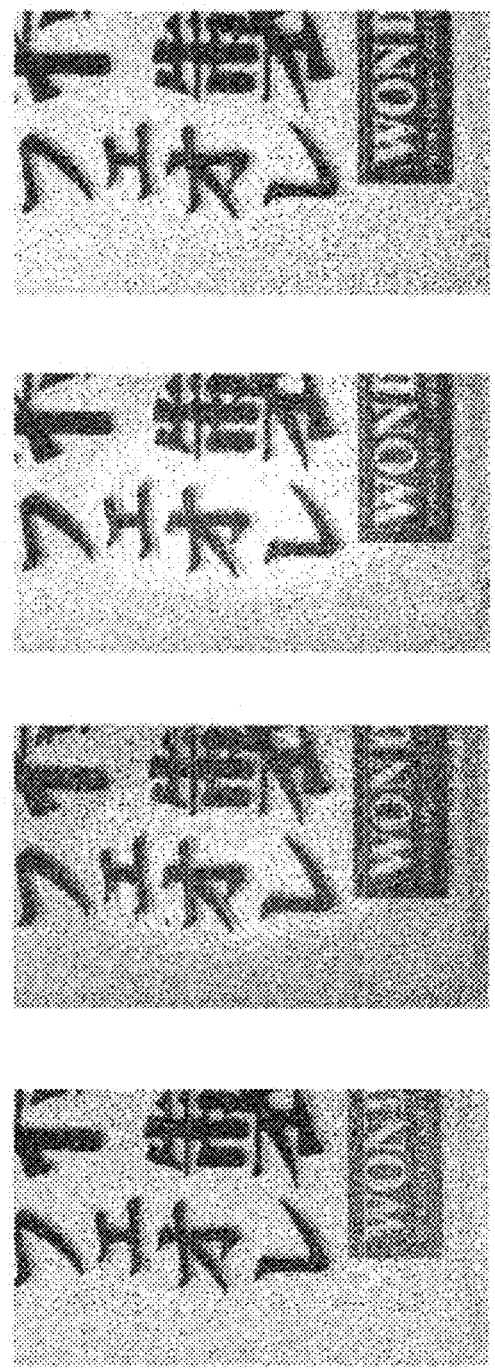

LATENT FINGERPRINT DETECTION METHOD, HEATING EVAPORATION DEVICE FOR DETECTING LATENT FINGERPRINT, LATENT FINGERPRINT DETECTION APPARATUS, AND COMPOSITION FOR DETECTING LATENT FINGERPRINT

TECHNICAL FIELD

The present invention relates to a latent fingerprint detection method, a heating evaporation device for detecting a latent fingerprint, a latent fingerprint detection apparatus, and a composition for detecting a latent fingerprint.

BACKGROUND ART

A latent fingerprint is one in which the shape of raised portions of skin (fingerprint ridges) with secretion attached thereto at a fingertip or the like are transferred to a specimen, such as a piece of evidence. The latent fingerprint contains, besides moisture that is the main ingredient, salt such as sodium chloride, lactic acid, amino acids, uric acid, protein, and vitamins. A latent fingerprint detection becomes an evidential matter necessary for determining, arresting, and prosecuting a criminal, thus being an important means for criminal investigation.

Conventional methods for detecting a latent fingerprint employ chemical reaction and physical adsorption reaction with fingerprint ingredients. Specifically, there are a powder method in which fine powder of aluminum, lycopodium, or the like is attached to moisture or fat in the fingerprint ingredients so as to use a color tone difference between the specimen and the powder, and a liquid method in which amino acid and salt contained in the fingerprint ingredients are reacted with chemicals so as to cause coloration.

With the powder method, the surface of the specimen to which a fingerprint is attached or the fingerprint seems to be attached is lightly brushed with a brush dusted with aluminum powder so that the aluminum powder is attached to the fingerprint, and the fingerprint is transferred to a gelatin sheet. However, in the process of applying the fine powder of aluminum or the like to the entirety of a region including the latent fingerprint, other fingerprint or the like may be mixed and contaminated, thus being obstructive to the case of conducting a DNA test after detecting the fingerprint. In the criminal investigation, if the specimen is a specific material, for example, a metal murder weapon such as pistol and knife, a synthetic leather, and an adhesive surface of a tape, it may be difficult to transfer a clear fingerprint.

With the liquid method, a specimen with a latent fingerprint needs to be immersed in a chemical solution, and hence it is unsuitable for detecting a fingerprint at a location that cannot be moved, such as walls. There are also the problems that the latent fingerprint may be washed away with the chemical solution, and that the specimen including the latent fingerprint may also be stained. It is therefore desired to achieve a technology of surely detecting the fingerprint without directly contacting the specimen.

As a detection method in place of the powder method or the liquid method, there is, for example, a fingerprint detection method (cyanoacrylate method) using 2-cyanoacrylic acid ester (monomer), which is one of gas methods suitable for a weak latent fingerprint and a specimen that is apt to change with a solvent or the like. The cyanoacrylate method has already been put to practical use in Japan and overseas. The cyanoacrylate method is intended for actualizing the latent fingerprint by polymerizing the 2-cyanoacrylic acid ester on the latent fingerprint region so as to form white solidification. The cyanoacrylate method is capable of restoring a clearer fingerprint trace, however, it may be difficult to ensure detection on a whitish specimen, such as a shopping bag and aluminum foil, because 2-cyanoacrylic acid ester polymerized on the latent fingerprint is transparent or white.

Hence, in order to improve the disadvantage of the cyanoacrylate method, a method has been proposed which includes bringing a fluorescent aye into contact during or after the 2-cyanoacrylic acid ester processing.

For example, with the fingerprint detection method disclosed in Patent Document 1, after the evaporated 2-cyanoacrylic acid ester is brought into contact with the surface of a test object so as to be gradually deposited thereon, a solution in which a fluorescent dye is dissolved in an organic solvent is brought into contact with the specimen, and the solution on the surface of the test object is dried, thereby detecting a fingerprint as a fluorescent fingerprint.

With the fingerprint detection method disclosed in Patent Document 2, a specimen having a fingerprint detected thereon is exposed to vaporization atmosphere of 2-cyanoacrylic acid ester and a sublimation dye, thereby detecting a colored fingerprint image.

With the polymer for detecting a fingerprint, the method for producing the same, the composition for detecting a fingerprint, and the fingerprint detection method using them, which are disclosed in Patent Document 3, 2-cyanoacrylic acid ester is polymerized using a specific fluorescent dye as a polymerization initiator, thus allowing the 2-cyanoacrylic acid ester and the fluorescent dye to be attached to a latent fingerprint at a low depolymerization temperature in a single step. This ensures a clear fluorescence detection even on the whitish specimen, such as the shopping bag and aluminum foil, which have been difficult to detect so far.

PRIOR ART DOCUMENTS

Patent Documents

Patent Document 1: Japanese Unexamined Patent Publication No. 2-268744
Patent Document 2: Japanese Unexamined Patent Publication No. 11-9575
Patent Document 3: WO 2008/044494

SUMMARY OF THE INVENTION

Problems to be Solved by the Invention

However, Patent Document 1 requires a two-stage processing in which the gasified 2-cyanoacrylic acid ester is attached to the latent fingerprint, followed by processing with the solution. When a specimen, such as plastic, is used, it is unavoidable that the specimen is altered due to the organic solvent. In addition, the flammability and toxicity of the organic solvent becomes an issue. The fingerprint detection method as disclosed in Patent Document 2 uses both the 2-cyanoacrylic acid ester and the dye, and hence there is the problem that such a basic dye as to polymerize the 2-cyanoacrylic acid ester cannot be used, and the usable dye is limited. From the viewpoints of storage stability and on-site handling properties, it is not preferable to use both the 2-cyanoacrylic acid ester and the dye. The fingerprint detection method as disclosed in Patent Document 3 has satisfactory handling properties because of the use of 2-cyanoacrylic acid ester polymer. However, the depolymerization of the 2-cyanoacrylic acid ester polymer requires high temperatures of approximately 170-210° C., thus making it difficult to stably gasify and evaporate by a simple device. Additionally, the DNA of a latent fingerprint may be damaged because ultraviolet is used for detection. When a specific wavelength light is used for detecting the fluorescent fingerprint, depending on the specimen, the specimen itself including the latent fingerprint may develop a color, thus making it difficult to achieve the detection.

As a means for gasifying (vaporizing) the 2-cyanoacrylic acid ester, there is employed a method in which the 2-cyanoacrylic acid ester is gasified by heating with a heater or the like. The use of flames makes it possible to reach high temperatures in a short time, however, may cause a fire. The use of the heater needs to ensure, for example, a stationary power source, thus contributing to deterioration of detection efficiency.

The present invention has been made in view of the above circumstances, and an object thereof is to provide a latent fingerprint detection method that is easy to handle and is capable of clearly detecting a latent fingerprint, and a heating evaporation device for detecting a latent fingerprint and a latent fingerprint detection apparatus, by which a chemical agent is heated at high temperatures in a short time so as to detect a clear latent fingerprint by a single operation, as well as a composition for detecting a latent fingerprint.

Means for Solving the Problem

The above object according to the present invention is achievable with the following means.

(1) A latent fingerprint detection method includes a heating step of heating a chemical agent to be gasified by heating so as to attach to a latent fingerprint on a specimen, and an exposure step of exposing a specimen having the latent fingerprint attached thereto to an atmosphere of the gasified chemical agent. The chemical agent is a mixture of a 2-cyanoacrylic acid ester polymer and a dye.

(2) In the latent fingerprint detection method as described in the above (1) the dye is an anthraquinone-based dye or naphthalimide-based dye. The method includes a light irradiation step of irradiating visible light to a fingerprint raised on the surface of the specimen.

(3) In the latent fingerprint detection method as described in the above (2), the anthraquinone-based dye is at least one selected from the group consisting of amino anthraquinone, amino hydroxyanthraquinone, diamino anthraquinone, dihydroxy anthraquinone, and diaminodihydroxy anthraquinone, and the naphthalimide-based dye is at least one selected from the group consisting of alkyl naphthalimide, alkoxy naphthalimide, alkoxyalkyl naphthalamide, amino naphthalimide, alkylamino naphthalimide, nitro naphthalimide, halogenated naphthalimide, carbonyl naphthalimide, phenylthio naphthalimide, cyano naphthalimide, and hydroxy naphthalimide.

(4) In the latent fingerprint detection method as described in any one of the above (1) to (3), the 2-cyanoacrylic acid ester polymer is obtained by polymerizing alkyl 2-cyanoacrylate having an alkyl group with a carbon number of 1 to 4.

(5) In the latent fingerprint detection method as described in any one of the above (1) to (4), the 2-cyanoacrylic acid ester polymer is polymerized using a water-containing alcohol.

(6) In the latent fingerprint detection method as described in any one of the above (1) to (5), the heating step includes heating using a heating evaporation device for detecting a latent fingerprint which includes the chemical agent, a chemical agent storage part to store the chemical agent therein, and a heat generator that includes the chemical agent storage part to store a hydrolysis exothermic agent therein.

(7) A heating evaporation device for detecting a latent fingerprint is intended to conduct the latent fingerprint detection method described in any one of the above (1) to (6). The heating evaporation device includes a chemical agent to be gasified by heating so as to attach to a latent fingerprint on a specimen, a chemical agent storage part to store the chemical agent therein, and a heat generator that includes the chemical agent storage part to store a hydrolysis exothermic agent therein.

(8) In the heating evaporation device for detecting a latent fingerprint as described in the above (7), the chemical agent is heated by the hydrolysis exothermic agent to 350° C. or more in one minute after starting heating.

(9) A latent fingerprint detection apparatus includes the heating evaporation device for detecting a latent fingerprint described in the above (7) or (8), and a storage case to store therein a specimen having a latent fingerprint attached thereto. The chemical agent is to be gasified by the heating evaporation device for detecting a latent fingerprint so as to allow the gasified chemical agent to fill the storage case.

(10) A composition for detecting a latent fingerprint contains a 2-cyanoacrylic acid ester polymer and a dye. The dye is an anthraquinone-based dye or naphthalimide-based dye.

Effect of the Invention

The latent fingerprint detection method according to the present invention is easy to handle and capable of clearly detecting a latent fingerprint. Further, the latent fingerprint is detectable in a visible light region, thus causing no DNA damage to the latent fingerprint. The latent fingerprint is obtainable as a fluorescent fingerprint image, thereby ensuring that a specimen with a fine pattern and a latent fingerprint attached to a wrinkled specimen, such as a plastic bag, are also clearly detectable.

With the heating evaporation device for detecting a latent fingerprint and the latent fingerprint detection apparatus according to the present invention, even a chemical agent, which is not gasified with a conventional method, is heated at high temperatures in a short time so as to be evaporated by using neither flames nor a power source, thereby ensuring that a clearer latent fingerprint is detectable anywhere.

The composition for detecting a latent fingerprint according to the present invention is excellent in storage stability.

The foregoing is a brief description of the present invention. The details of the present invention are further clarified by reading embodiments for carrying out the present invention described below (hereinafter referred to as "embodiments") with reference to the accompanying drawings.

BRIEF DESCRIPTION OF THE DRAWINGS

FIGS. 10(a) to 10(d) are images of fluorescent fingerprints obtained in Comparative Example 1;

FIGS. 11(a) to 11(e) are images of fluorescent fingerprints obtained in Example 2;

FIGS. 12(a) to 12(d) are images of fluorescent fingerprints obtained in Example 3;

PREFERRED EMBODIMENTS FOR CARRYING OUT THE INVENTION

Figure 1:
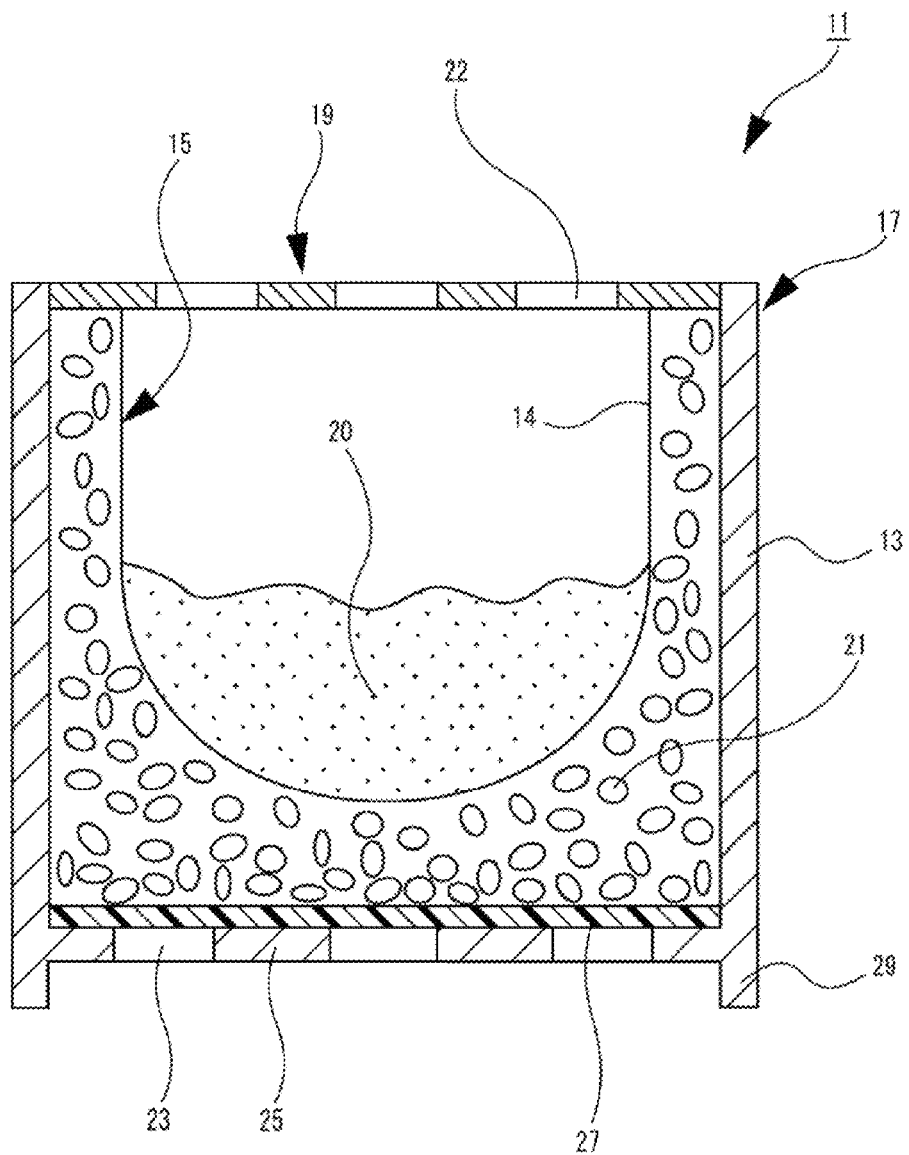
FIG. 1 is a longitudinal sectional view of a heating evaporation device for detecting a latent fingerprint according to a first embodiment of the present invention.

A latent fingerprint detection method according to the present invention includes a heating step of heating a chemical agent to be gasified by heating so as to attach to a latent fingerprint on a specimen, and an exposure step of exposing the specimen having the latent fingerprint attached thereto to an atmosphere of the gasified chemical agent. The chemical agent is a mixture of a 2-cyanoacrylic acid ester polymer and a dye (hereinafter also referred to as "a composition for detecting a latent fingerprint).

The 2-cyanoacrylic acid ester polymer for use in the present invention is one in which a generally used 2-cyanoacrylic acid ester (monomer) is polymerized onto an adhesive composition or the like. Examples of the 2-cyanoacrylic acid ester include esters, such as methyl, ethyl, chloroethyl, n-propyl, i-propyl, allyl, propargyl, n-butyl, i-butyl, n-pentyl, n-hexyl, cyclohexyl, phenyl, tetrahydrofurfuryl, heptyl, 2-ethylhexyl, n-octyl, 2-octyl, n-nonyl, oxononyl, n-decyl, n-dodecyl, methoxyethyl, methoxypropyl, methoxyisopropyl, methoxybutyl, ethoxyethyl, ethoxypropyl, ethoxy isopropyl, propoxymethyl, propoxyethyl, isopropoxyethyl, propoxypropyl, butoxymethyl, butoxyethyl, butoxypropyl, butoxyisopropyl, butoxybutyl, 2,2,2-trifluoroethyl, and hexafluoroisopropyl. Only one kind or two or more kinds of these 2-cyanoacrylic acid esters may be used together. Of these, alkyl 2-cyanoacrylate is preferred, and alkyl 2-cyanoacrylate having an alkyl group with a carbon number of 1 to 4 is more preferred because of high reactivity with respect to moisture or the like in a latent fingerprint.

The 2-cyanoacrylic acid ester polymer is producible by subjecting 2-cyanoacrylic acid ester as a monomer to polymerization reaction. Although the polymerization of 2-cyanoacrylic acid ester can be conducted using water, alcohol, or a basic compound as a polymerization initiator, water or alcohol is preferred, and water-containing alcohol is more preferred in the present invention. As the alcohol, it is possible to use an optional alcohol, such as methanol, ethanol, or isopropanol.

The 2-cyanoacrylic acid ester polymer may have any shape, but a powder-shape is preferred because efficient depolymerization is ensured in the heating step. The powder-shaped 2-cyanoacrylic acid ester polymer is producible by, for example, dissolving in acetone the 2-cyanoacrylic acid ester polymer polymerized using the water-containing alcohol, and by reprecipitating with methanol, followed by suction filtration and drying under reduced pressure.

The dye for use in the present invention is preferably a sublimation dye having high thermal stability and a wide excitation region. Particularly, fluorescent pigments, such as anthraquinone-based dyes and naphthalimide-based dyes, are more suitably used because these have excellent absorption properties in a visible light region so as to ensure a clear detection of a latent fingerprint. Specific examples of the anthraquinone-based dyes include amino anthraquinone, amino hydroxy anthraquinone, diamino anthraquinone, dihydroxy anthraquinone, and diaminodihydroxy anthraquinone. Specific examples of the naphthalimide-based dyes include alkyl naphthalimide, alkoxy naphthalimide, alkoxyalkyl naphthalimide, amino naphthalimide, alkylamino naphthalimide, nitro naphthalimide, halogenated naphthalimide, carbonyl naphthalimide, phenylthio naphthalimide, cyano naphthalimide, and hydroxy naphthalimide.

In the present invention, these dyes can be washed with acid before being mired with the 2-cyanoacrylic acid ester polymer. This ensures removal of an extremely small amount of impurities, such as a basic compound, attached to the surface of the dye.

The acid to wash the dye is preferably sulfonic acid or halogenated carboxylic acid. Specific examples of the acid include aryl sulfonates, such as benzenesulfonic acid and p-toluenesulfonic acid, alkyl sulfonic acids, such as methanesulfonic acid and ethanesulfonic acid, and halogenated carboxylic acids, such as trichloroacetic acid and trifluoroacetic acid. These acids are used as a dilute solution (0.1-5% by mass concentration), such as water, toluene, methanol, and acetone.

The content of the 2-cyanoacrylic acid ester polymer in the composition for detecting a latent fingerprint according to the present invention is preferably 10-90% by mass, more preferably 10-70% by mass, and particularly preferably 10-50% by mass. The clear detection of the latent fingerprint is ensured when the content of the 2-cyanoacrylic acid ester polymer is in the above-mentioned range.

The content of the dye in the composition for detecting a latent fingerprint is not particularly limited as long as the effect of the present invention is not impaired. The content of the dye needs to be 1% by mass or more, preferably 10% by mass or more, more preferably 50% by mass, and particularly preferably 60-90% by mass with respect to a total amount of the 2-cyanoacrylic acid ester polymer and the dye. When the content of the dye is 50% by mass or more with respect to the total amount of the 2-cyanoacrylic acid ester polymer and the dye, the clear detection of a fingerprint is ensured even after time has passed after the chemical agent was attached to the latent fingerprint, while ensuring more excellent reducibility of the fingerprint.

In the mixture obtained by mixing the 2-cyanoacrylic acid ester polymer and the dye in the present invention, the volatilization temperature of the dye is lowered due to the heating. This seems to be because 2-cyanoacrylic acid ester generated by the depolymerization is vaporized, thereby facilitating volatilization of the dye. Consequently, the volatilization temperature of the entirety of the composition for detecting a latent fingerprint can be set low.

In the present invention, the composition for detecting a latent fingerprint may contain ingredients other than the 2-cyanoacrylic acid ester polymer and the dye as long as the effect of the present invention is producible. Examples of the ingredients include stabilizer, plasticizer, and thickener.

The latent fingerprint detection method according to the present invention has the heating step and the exposure step as described earlier.

The heating step is to heat the mixture of the 2-cyanoacrylic acid ester polymer and the dye so as to generate gases (vapors) of 2-cyanoacrylic acid ester and the dye. The 2-cyanoacrylic acid ester polymer is depolymerized by heating, thereby generating the gas of the 2-cyanoacrylic acid ester.

The heating in the heating step can be carried out by flames, a hotplate device, or a device with a heating part. Particularly, a heating method using a hydrolysis heating agent is preferred because a high-temperature heating can be achieved in a short time without using flames or a power source. The hydrolysis heating agent is a material that generates heat by itself upon reaction with water. Examples of the hydrolysis heating agent include calcium oxide (quicklime), magnesium chloride, aluminum chloride, calcium chloride, and iron chloride.

The exposure step is to bring the specimen into contact with the gases of the 2-cyanoacrylic acid ester and the dye which are to be generated in the heating step. During the exposure step, the 2-cyanoacrylic acid ester is polymerized onto a latent fingerprint region on the specimen using, as a polymerization initiator, the moisture that is the main ingredient of the latent fingerprint region, and the dye is selectively adsorbed onto the latent fingerprint, thereby obtaining a fluorescent fingerprint image. In the exposure step, the gases of the 2-cyanoacrylic acid ester and the dye may be directly sprayed to the specimen so as to ensure the contact therebetween. However, the exposure step is preferably conducted in a storage case filled with the gases in order to efficiently bring the gases into contact with the specimen.

The present invention preferably includes a light irradiation step of irradiating visible light onto the fingerprint raised on the surface of the specimen by the exposure step. The visible light is an electromagnetic wave having a wavelength of approximately 400-800 nm. A light irradiation source is not particularly limited as long as it can irradiate an effective amount of light. A general irradiation source is usable, and examples thereof include the following irradiation sources: carbon arc, mercury vapor arc, fluorescent lamp, argon glow lamp, incandescent lamp, halogen lamp, high pressure mercury lamp, ultra-high pressure mercury lamp, high pressure mercury lamp, low pressure mercury lamp, xenon short lamp, high power water-cooled xenon lamp, xenon flash lamp, and metal halide lamps, such as gallium halide lamp and thallium halide lamp. It is also possible to attach a filter to the irradiation source in order to irradiate light having a desired wavelength onto the fingerprint image, thereby obtaining a fluorescent fingerprint image. The fluorescent fingerprint image thus obtained is preserved by being photographed using a digital camera or the like through the filter that cuts the wavelength of irradiation light.

The composition for detecting a latent fingerprint according to the present invention ensures obtaining a clear fingerprint image even from an old fingerprint having little moisture after the passage of time. This seems to be because the dye also melts into the fatty acid of the latent fingerprint and generates fluorescence.

With the conventional cyanoacrylate method, a large amount of 2-cyanoacrylic acid aster is polymerized onto and adhered to a latent fingerprint. Therefore, the whitened 2-cyanoacrylic acid ester polymer is strongly adhered to the specimen, and it is necessary to use an organic solvent, such as acetone, or cut off the polymerized part in order to wipe off the polymerized body. Hence, for example, a specimen made of plastic may be unreturnable to the original state. On the other hand, the composition for detecting a latent fingerprint according to the present invention has excellent reducibility. Such a small amount of the 2-cyanoacrylic acid ester polymer, which is a visible lower limit or less, is used together with the dye so as to increase the amount, thus permitting visualization and detection. This minimizes the attachment of the 2-cyanoacrylic acid ester polymer to the latent fingerprint, thus preventing the attachment to unnecessary parts. Moreover, because the composition for detecting a latent fingerprint is powder, a necessary and sufficient amount of a reagent to be gasified according to an exposure volume can be used quantitatively. Hence, the 2-cyanoacrylic acid ester polymer is less apt to be whitened, and therefore the fingerprint ridges are not thickened, thus enhancing detectability of the fingerprint.

The fingerprint detection using the composition for detecting a latent fingerprint according to the present invention eliminates the need for a fingerprint detection using ultraviolet. Therefore, after detecting the fingerprint, the fingerprint is lifted while being confirmed by a wavelength variable light source. This ensures that a non-damaged DNA is liftable from the fingerprint attached to the specimen.

Embodiments of the latent fingerprint detection apparatus for conducting the latent fingerprint detection method according to the present invention are described below with reference to the drawings.

FIG. 1 is a longitudinal sectional view of a heating evaporation device 11 for detecting a latent fingerprint according to a first embodiment of the present invention.

As shown in FIG. 1, the heating evaporation device 11 for detecting a latent fingerprint according to the first embodiment includes a heat generator 17 made up of a bottomed cylindrical outer container 13 and a chemical agent storage part 15 partitionally formed inside the outer container 13 by a partition member 14.

A hydrolytic exothermic agent 21 is stored in the heat generator 17 so as to exist from the bottom to the side of the outer container 13. The bottom of the heat generator 17 is closed by a bottom plate 25 having a water passage hole 23, and the water passage hole 23 is closed by an unwoven sheet 27 that is the member having water permeability. The partition member 14 has a side wall having a cylindrical shape and a bottom that is hollow and has an approximately hemispherical shape. The side wall is disposed coaxially with a circumferential wall of the outer container 13.

An upper open surface of the heat generator 17 is covered with a lid member 19 having a plurality of openings formed in a region corresponding to an upper open surface of the partition member 14. The openings of the lid member 19 are closed by a hot-melt film 22.

The hydrolytic exothermic agent 21 is allowed to fill a space formed by the circumferential wall of the outer container 13, the partition member 14, and the unwoven sheet 27. A powder chemical agent 20, which is to be gasified by heating so as to attach to the latent fingerprint on a specimen 41, is stored in a chemical agent storage part 15 partitionally formed inside the partitioned member 14.

Leg parts 29 are disposed on the bottom of the heat generator 17, and a clearance is formed below the bottom plate 25 so as to allow water to flow therethrough.

The outer container 13 that is a component member of the heat generator 17 is not particularly limited as long as it has heat resistance to the heating temperature of the hydrolysis exothermic agent 21 stored inside the heat generator 17. There are, for example, heat-resistant plastic container, paper container, metal container, ceramic container, and glass container. The outer container 13 is preferably has a diameter of 5 cm or more, more preferably 5-10 cm. The height of the heat generator 17 preferably has a height of 2-9 cm, more preferably 3-8 cm. The outer container 13 preferably has a volume of 40 $cm^3$ or more, more preferably 100-480 $cm^3$.

The hydrolytic exothermic agent 21 is the material that generates heat by itself upon reaction with water. It is possible to use, for example, calcium oxide (quicklime), magnesium chloride, aluminum chloride, calcium chloride, and iron chloride. The heating temperature is preferably 250-450° C. The content of the hydrolytic exothermic agent 21 in the first embodiment is approximately 40-400 g, for example, when using calcium oxide, and the hydrolytic exothermic agent 21 is allowed to fill the entire interior of the heat generator 17 which is partitionally formed by the partitioned member 14. This configuration ensures that the chemical agent 20 loaded in the chemical agent storage part 15 can be heated to 350° C. or more by the hydrolytic exothermic agent 21 in at least one minute after starting heating.

Figure 2:
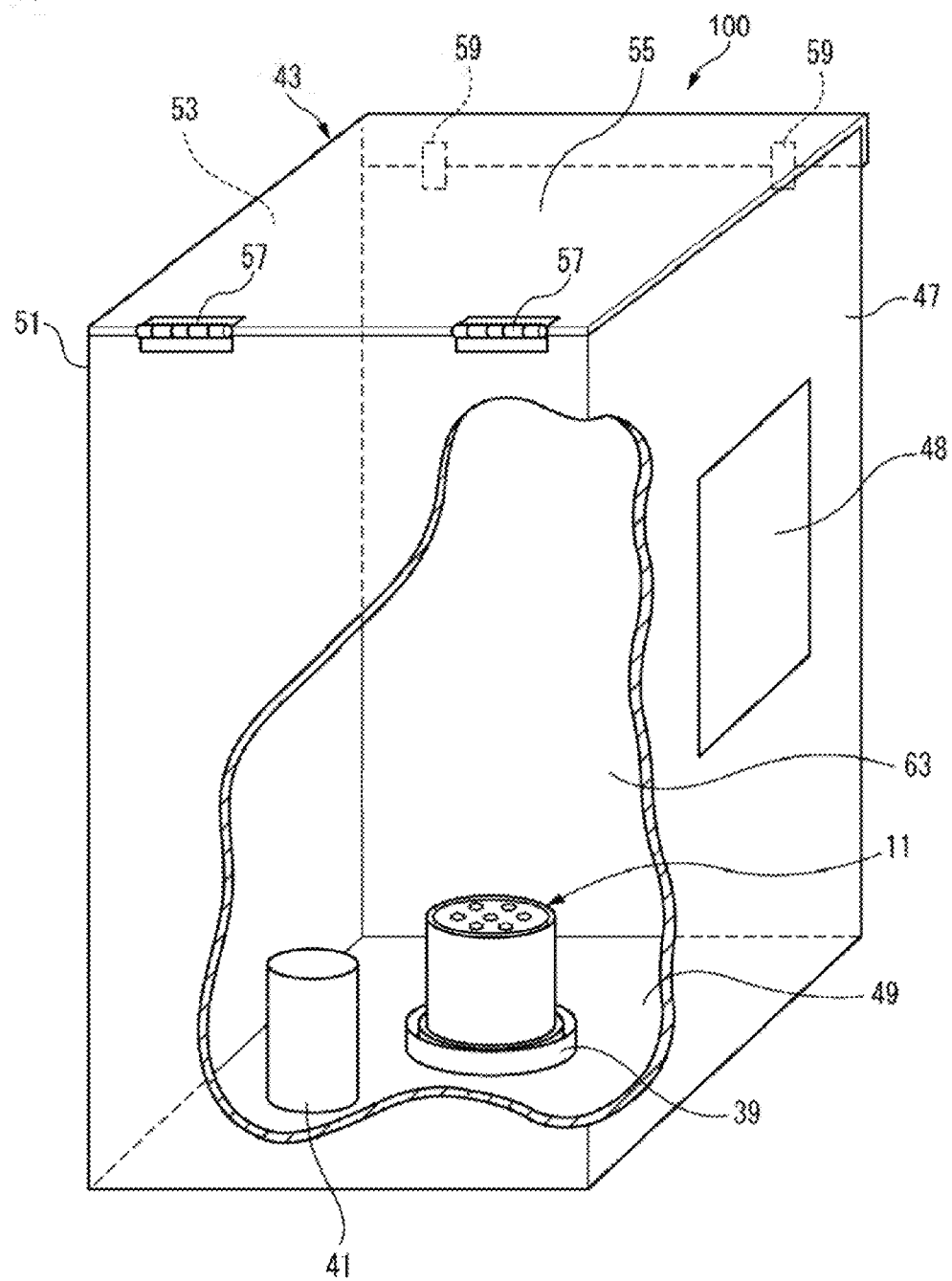
FIG. 2 is a partially cut-away perspective view showing a latent fingerprint detection apparatus according to a second embodiment of the present invention which uses the heating evaporation device for detecting a latent fingerprint shown in FIG. 1.

When using the heating evaporation device 11 for detecting a latent fingerprint in the first embodiment, the heating evaporation device 11 for detecting a latent fingerprint is immersed in a water-filled water supply container 39 (see FIG. 2). Then, the water flows from the clearance formed by the leg parts 29 of the heat generator 17 and enters through the water passage holes 23 disposed on the bottom of the outer container 13. The water contacts the hydrolysis exothermic agent 21, and by the heat of reaction occurred at that time, the chemical agent 20 in the chemical agent storage part 15 is heated, gasified, and evaporated. Consequently, the hot-melt film 22 is melted and discharged to the outside (into a specimen storage part 63 of the storage case 43) through the openings of the lid member 19. The hot-melt film 22 is thermally melted by the heat dissipation from the hydrolysis exothermic agent 21, the heat of the outer container 13, and the contact with the evaporated chemical agent 20. Therefore, from a relatively early time of the evaporation, the evaporated chemical agent 20 is efficiently released outside through the openings of the lid member 19.

In the present embodiment, the composition for detecting a latent fingerprint described earlier is used as the chemical agent 20 to be loaded in the chemical agent storage part 15.

The heat generator 17 heats the chemical agent 20 to be loaded in the chemical agent storage part 15 so as to generate a mixed gas of the 2-cyanoacrylic acid ester (monomer) and the dye, With the heating evaporation device 11 for detecting a latent fingerprint according to the first embodiment, the chemical agent 20 stored in the chemical agent storage part 15 is gasified and evaporated by heating so as to attach to the latent fingerprint on the specimen. Temperature control and the like are complicated when the 2-cyanoacrylic acid ester having extremely high activity is used as in the conventional cyanoacrylate method. On the other hand, the present invention employs the 2-cyanoacrylic acid ester polymer and hence ensures improvement in handling properties and stability, such as temperature control and quantitativity of the chemical agent 20. Additionally, the use of the heat generator 17 of the present invention ensures complete depolymerization of various kinds of 2-cyanoacrylic acid ester polymers.

Next, a description is given of the operation of the heating evaporation device 11 for detecting a latent fingerprint, which has the foregoing configuration.

The heating evaporation device 11 for detecting a latent fingerprint according to the first embodiment is capable of rapidly heating the chemical agent 20 loaded in the chemical agent storage part 15 by ensuring that it reaches high temperatures, for example, 250-450° C. in three minutes by the heat generator 17 using the heat of reaction of the hydrolysis exothermic agent 21 that heats by itself upon reaction with water. The chemical agent 20 is heated by the hydrolysis exothermic agent 21 to 350° C. or more in at least one minute after starting heating, and quickly reaches high temperatures in a short time, thus generating a high-concentration mixed gas of the 2-cyanoacrylic acid ester and the dye.

Moreover, the heat generator 17 heats the 2-cyanoacrylic acid ester and the dye at the high temperatures of 350° C. or more, thereby ensuring the gasification and evaporation of the 2-cyanoacrylic acid ester polymer and the dye which differ in polymerization degree. In addition, the vapor generated from the heat generator 17 facilitates the polymerization of the 2-cyanoacrylic acid ester attached to the latent fingerprint and the whitening of the produced 2-cyanoacrylic acid ester polymer. It is therefore possible to actualize a clear latent fingerprint even when detecting a fingerprint in a wide space, and even under extremely dry conditions.

Subsequently, by exposing the specimen 41 (see FIG. 2) to the mixed gas atmosphere of the 2-cyanoacrylic acid ester and the dye, the polymerization of the 2-cyanoacrylic acid ester and the adsorption of the dye occur selectively on the latent fingerprint on the specimen 41, thereby obtaining a dyed (fluorescent) fingerprint image.

Next, a description is given of a latent fingerprint detection apparatus 100 and a latent fingerprint detection method according to a second embodiment using the foregoing heating evaporation device 11 for detecting a latent fingerprint.

FIG. 2 is a partially cut-away perspective view showing the latent fingerprint detection apparatus 100 according to the second embodiment using the heating evaporation device 11 for detecting a latent fingerprint shown in FIG. 1.

The latent fingerprint detection method according to the present embodiment may use only the heating evaporation device 11 for detecting a latent fingerprint, but preferably uses the latent fingerprint detection apparatus 100 shown in FIG. 2. This ensures that the polymerization of 2-cyanoacrylic acid ester and the adsorption of the dye are quantitatively and efficiently carried out with respect to the latent fingerprint on the specimen 41.

The latent fingerprint detection apparatus 100 of the second embodiment includes the heating evaporation device 11 for detecting a latent fingerprint, and the storage case 43 as described above. The storage case 43 stores therein the heating evaporation device 11 for detecting a latent fingerprint, and the specimen 41. The gasified 2-cyanoacrylic acid ester and the gasified dye are allowed to fill the storage case 43 by heating the chemical agent 20 in the heating evaporation device 1 for detecting a latent fingerprint.

The storage case 43 is a box having a rectangular parallelepiped shape, and includes a body 51 made up of a side wall 47 and a bottom wall 49, and a lid body 55 that serves as a top plate and closes an upper opening 53 of the body 51. The heating evaporation device 11 for detecting a latent fingerprint is put in the water-filled water supply container 39, and is disposed on the bottom wall 49 of the storage case 43.

The lid body 55 of the storage case 43 includes a flat plate part having approximately the same shape as the upper opening 53 of the body 51, a hinge 57 connected to the upper opening 53 so as to permit rotation of one side of the flat plate part, and a hook 59 that is disposed on the side wall 47 on the opposite side of the hinge 57, and locks an opening-closing end of the lid body 55. The side wall 47 of the storage case 43 includes a transparent window 48 that permits observation of the interior of the storage case 43. The storage case 43 thus configured has predetermined air tightness under the condition that the lid body 55 closing the upper opening 53 is locked by the hook 59. The specimen storage part 63 is located above the bottom wall 49 in the interior of the storage case 43, and the specimen 41 is stored in the specimen storage part 63.

In the latent fingerprint detection apparatus 100 shown in FIG. 2, the columnar specimen 41 is directly mounted on the bottom wall 49. The specimen 41 may be suspended from a hook shank or the like hanged on the side wall 47, depending on the type and shape of the specimen 41.

Alternatively, a punching metal (plate body) having a plurality of through holes, a metal mesh, or the like is disposed in the interior of the storage case 43, and the specimen 41 may be mounted thereon. In this case, the heating evaporation device 11 for detecting a latent fingerprint can be stored in a lower part of the specimen storage part 63.

The material for forming the storage case 43 is not particularly limited as long as it has heat resistance to such an extent as not to be melted and deformed by heat. For example, corrugated cardboard, metals, such as aluminum alloy, copper alloy, steel, and stainless steel, and engineering plastics, such as polyethylene terephthalate, polybutylene terephthalate, and polycarbonate, may be used. Contamination or the like due to other specimen is preventable by using a disposable storage case made of a corrugated cardboard or the like.

When detecting a latent fingerprint on the specimen 41, firstly, the lid body 55 of the storage case 43 is opened, and the specimen 41 is inserted from the upper opening 53 and mounted on the bottom wall 49. Therefore, the heating evaporation device 11 for detecting a latent fingerprint is immersed in the water supply container 39 which is filled with water in advance and is mounted on the bottom wall 49. Then, the lid body 55 is fixed by the hook 59 so as to close the upper opening 53.

In the heating step of the latent fingerprint detection method according to the present embodiment, the chemical agent 20 that is the composition for detecting a latent fingerprint, which is a mixture of the 2-cyanoacrylic acid ester and a specific dye, is heated by the hydrolysis heating agent 21 in the heat generator 17.

In the exposure step, the heating of the 2-cyanoacrylic acid ester polymer and the dye causes stably and effectively the depolymerization and gasification of the 2-cyanoacrylic acid ester polymer and the gasification of the dye, and the generated mixed gas of the 2-cyanoacrylic acid ester and the dye is allowed to evaporate and fill the storage case 43. Accordingly, the specimen 14 is exposed to the atmosphere of the gasified 2-cyanoacrylic acid ester and the gasified dye.

This ensures that the 2-cyanoacrylic acid ester and the dye evaporated by the heating evaporation device 11 for detecting a latent fingerprint, and the vapor is attached to the latent fingerprint on the specimen 41. That is, in the storage case 43 filled with the mixed gas of the 2-cyanoacrylic acid ester and the dye, the 2-cyanoacrylic acid ester is polymerized (repolymerized) in the latent fingerprint region on the specimen 41 by using, as a catalyst, basic ingredients and moisture that are the main ingredients of the latent fingerprint, and at the same time, the dye is selectively adsorbed onto the latent fingerprint region, thereby forming a dyed fingerprint (specifically, a fluorescent fingerprint). By jetting the vapor together with the gasified chemical agent 20, a clear fingerprint is detectable even when the fingerprint is detected in a wide space, and under a dry condition.

Thus, the latent fingerprint detection apparatus 100 and the latent fingerprint detection method according to the second embodiment require neither flames for volatilizing the chemical agent 20 nor a heater that needs a power source. Therefore, the latent fingerprint detection apparatus 100 can foe configured with a lightweight simple structure. This ensures that a clear latent fingerprint is simply detectable anywhere, thus facilitating on-site handling.

Hence, with the heating evaporation device 11 for detecting a latent fingerprint according to the first embodiment, and the latent fingerprint detection apparatus 100 and the latent fingerprint detection method according to the second embodiment, the clear latent fingerprint is detectable by heating the chemical agent 20 at high temperatures in the short time without using the flames or a power source.

Figure 3:
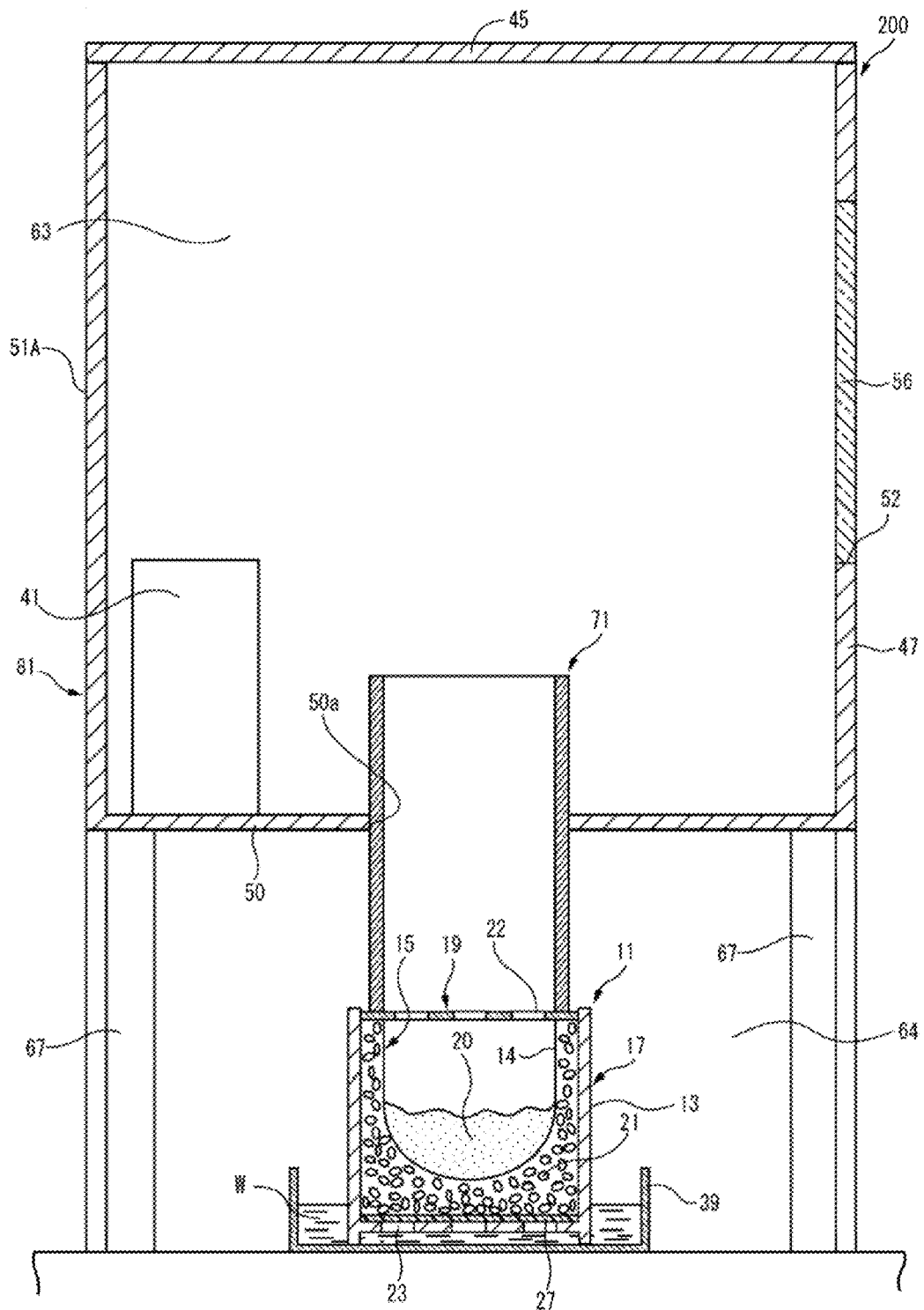
FIG. 3 is a longitudinal sectional view of a main part showing a latent fingerprint detection apparatus according to a third embodiment of the present invention which uses the heating evaporation device for detecting a latent fingerprint shown in FIG. 1.

FIG. 3 is a longitudinal sectional view of a main part showing a latent fingerprint detection apparatus 200 according to a third embodiment using the heating evaporation device 11 for detecting a latent fingerprint shown in FIG. 1. Component members similar to those of the latent fingerprint detection apparatus 100 of the second embodiment are identified by the same reference numerals, and their respective descriptions are omitted here.

The latent fingerprint detection apparatus 200 of the third embodiment includes the foregoing heating evaporation device 11 for detecting a latent fingerprint, and a storage case 81 to store the specimen 41 therein. The 2-cyanoacrylic acid ester and the dye, which are to be gasified by the heating evaporation device 11 for detecting a latent fingerprint, are allowed to evaporate and fill the storage case 81.

The storage case 81 of the third embodiment is a box having a rectangular parallelepiped shape, and includes a body 51A made up of a top plate 45, a side wall 47 and a bottom wall 50, and a lid body 56 that closes an opening 52 disposed on the side wall 47. The lid body 56 is made of a transparent acrylic plate, and also functions as a transparent window that permits observation of the interior of the storage case 81 through the opening 52.

The storage case 81 further includes leg parts 67 respectively vertically disposed at four corners of the lower surface of the bottom wall 50, and a heating evaporation device mounting space 64 disposed below the body 51A. A circular bottom surface opening 50a that permits insertion of a metal cylindrical pipe 71 is formed on a middle part of the bottom wall 50.

The upper end of the cylindrical pipe 71 passing through the bottom surface opening 50a projects in a specimen storage part 63, and the lower end thereof projects in the heating evaporation device mounting space 64, thereby permitting communication between the specimen storage part 63 and the heating evaporation device mounting space 64. If necessary, a packing is interposed between the bottom surface opening 50a and an outer peripheral wall of the cylindrical pipe 71 so as to keep air-tightness therebetween.

When detecting a latent fingerprint on the specimen 41, the lid body (transparent window) 56 of the storage case 81 is removed to open the opening 52, and the specimen 41 is entered through the opening 52 into the specimen storage part 63. After the specimen 41 is mounted on the bottom wall 50, the lid body (transparent window) 56 is fixed so as to close the opening 52.

The heating evaporation device 11 for detecting the latent fingerprint immersed in the water-filled water supply container 39 is disposed in the heating evaporation device mounting space 64. On this occasion, the upper end of the heating evaporation device 11 for detecting a latent fingerprint is engaged with a lower opening end of the cylindrical pipe 71. Consequently, the lower opening end of the cylindrical pipe 71 is closed by the heating evaporation device 11 for detecting a latent fingerprint, which is mounted at a predetermined position, thereby bringing the specimen storage part 63 in the storage case 81 into an air-tightly partitioned state.

With the latent fingerprint detection apparatus 200 of the third embodiment, the hydrolysis exothermic agent 21 in the heat generator 17 is to heat the chemical agent 20 (the mixture of the 2-cyanoacrylic acid ester polymer and the dye), which is gasified and attached to the latent fingerprint on the specimen 41 by being heated.

Here, the hydrolysis exothermic agent 21 in the heat generator 17 generates vapor together with heat of reaction, and the vapor is released into the heating evaporation device mounting space 64 that is outside the storage case 81, and does not flow in the air-tightly partitioned specimen storage part 63.

The heating of the 2-cyanoacrylic acid ester polymer and the dye causes stably and effectively the depolymerization and gasification of the 2-cyanoacrylic acid ester polymer and the gasification of the dye. Then, the generated mixed gas of the 2-cyanoacrylic acid ester and the dye is allowed to evaporate and fill the specimen storage part 63 of the storage case 81. Consequently, the specimen 41 is exposed to the atmosphere of the gasified 2-cyanoacrylic acid ester and the gasified dye.

That is, the latent fingerprint detection apparatus 200 of the third embodiment produces the operational advantage that only the mixed gas of the 2-cyanoacrylic acid ester and the dye, which contains no vapor evaporated by the heating evaporation device 11 for detecting a latent fingerprint, is attachable to the latent fingerprint on the specimen 41.

Therefore, when there is the possibility that excessive whitening of the 2-cyanoacrylic acid ester due to the vapor exerts adverse effect on the fingerprint detection, for example, when the 2-cyanoacrylic acid ester and the dye are allowed to attach to the latent fingerprint on the specimen 41 in a narrow space, a satisfactory latent fingerprint is detectable by using the latent fingerprint detection apparatus 200 of the third embodiment.

The component members, such as the chemical agent, the chemical agent storage part, the hydrolysis exothermic agent, the heat generator, and the storage case, in the heating evaporation device for detecting a latent fingerprint and in the latent fingerprint detection apparatus of the present invention are not limited to the configurations of the foregoing embodiments, but it is, of course, possible to employ various embodiments on the basis of the gist of the present invention.

For example, in the heating evaporation device 11 for detecting a latent fingerprint according to the first embodiment, the powder chemical agent 20 is stored in the chemical agent storage part 15. However, it should be understood that the present invention is not limited thereto. It is also possible to store, in the chemical agent storage part 15, a carrier in which a liquid chemical agent 20 is impregnated in a solid-state inorganic porous body, such as a clay, or a chemical agent that is previously mixed into a granule or tablet.

In the latent fingerprint detection apparatus 200 of the third embodiment, the opening 52 and the lid body (transparent window) 56 for loading and unloading the specimen 41 into and out of the storage case 81 are disposed on the side wall 41 of the body 51A. Alternatively, the opening may be disposed on the top plate 45 so that the lid body is openable and closable in an upper part of the storage case 81. Still alternatively, the transparent window is disposed on the top plate 45 so that the interior of the storage case 81 is observable from above the storage case 81.

Here, the features of the foregoing embodiments of the heating evaporation device for detecting a latent fingerprint, the latent fingerprint detection apparatus, and the latent fingerprint detection method according to the present invention are briefly summarized and listed in the following items [i] to [x].

[i] A latent fingerprint detection method includes a heating step of heating a chemical agent 20 to be gasified by heating so as to attach to a latent fingerprint on the specimen, and an exposure step of exposing the specimen 41 having the latent fingerprint attached thereto to the atmosphere of the gasified chemical agent 20. The chemical agent 20 is a mixture of a 2-cyanoacrylic acid ester polymer and a dye.

[ii] In the latent fingerprint detection method as described in the above [i], the dye is an anthraquinone-based dye or naphthalimide-based dye. The method includes a light irradiation step of irradiating visible light to a fingerprint raised on the surface of the specimen 41.

[iii] In the latent fingerprint detection method as described in the above [ii], the anthraquinone-based dye is at least one selected from the group consisting of amino anthraquinone, aminohydroxy anthraquinone, diamino anthraquinone, dihydroxy anthraquinone, and diaminodihydroxy anthraquinone, and the naphthalimide-based dye is at least one selected from the group consisting of alkyl naphthalimide, alkoxy naphthalimide, alkoxyalkyl naphthalimide, amino naphthalimide, alkylamino naphthalimide, nitro naphthalimide, halogenated naphthalimide, carbonyl naphthalimide, phenylthio naphthalimide, cyano naphthalimide, and hydroxy naphthalimide.

[iv] In the latent fingerprint detection method as described in any one of the above [i] to [iii], the 2-cyanoacrylic acid ester polymer is obtained by polymerizing alkyl 2-cyanoacrylate having an alkyl group with a carbon number of 1 to 4.

[v] In the latent fingerprint detection method as described in any one of the above [i] to [iv], the 2-cyanoacrylic acid, ester polymer is polymerized using a water-containing alcohol.

[vi] In the latent fingerprint detection method as described in any one of the above [i] to [v], the heating step includes heating using a heating evaporation device 11 for detecting a latent fingerprint which includes the chemical agent 20, a chemical agent storage part 15 to store the chemical agent 20 therein, and a heat generator 17 that includes the chemical agent storage part 15 to store a hydrolysis exothermic agent 21 therein.

[vii] A heating evaporation device 11 for detecting a latent fingerprint is intended to conduct the latent fingerprint detection method described in any one of the above [i] to [vi]. The heating evaporation device 11 includes a chemical agent 20 to be gasified by heating so as to attach to a latent fingerprint on a specimen 41, a chemical agent storage part 15 to store the chemical agent 20 therein, and a heat generator 17 that includes the chemical agent storage part 15 to store a hydrolysis exothermic agent 21 therein.

[viii] In the heating evaporation device 11 for detecting a latent fingerprint as described in the above [vii], the chemical agent 20 is heated by the hydrolysis exothermic agent 21 to 350° C. or more in one minute after starting heating.

[ix] A latent fingerprint detection apparatus 100 includes the heating evaporation device 11 for detecting a latent fingerprint described in the above [vii] or [viii], and a storage case 43 to store therein a specimen 41 having a latent fingerprint attached thereto. The chemical agent 20 is to be gasified by the heating evaporation device 11 for detecting a latent fingerprint so as to allow the gasified chemical agent 20 to fill the storage case 43.

[x] A composition for detecting a latent fingerprint contains a 2-cyanoacrylic acid ester polymer and a dye. The dye is an anthraquinone-based dye or naphthalimide-based dye.

With the latent fingerprint detection method having the configuration described in the above [i], it is easy to handle, and a clear latent fingerprint is detectable. Additionally, the latent fingerprint is detectable in the visible light region, thus causing no DNA damage to the latent fingerprint.

With, the latent fingerprint detection method having the configuration described in the above [ii], the mixed gas of 2-cyanoacrylic acid ester and the dye is generated by heating. By exposing the specimen to the atmosphere of the mixed gas of the 2-cyanoacrylic acid ester and the dye, the polymerization of the 2-cyanoacrylic acid, ester and the adsorption of the dye occur selectively on the latent fingerprint on the specimen, thereby obtaining a dyed fingerprint image by a one-time processing.

With the latent fingerprint detection method having the configuration described in the above [iii], the latent fingerprint is detectable more clearly.

With the latent fingerprint detection method having the configuration described in the above [iv], the latent fingerprint is detectable more surely.

With the latent fingerprint detection method having the configuration described in the above [v], the latent fingerprint is detectable more efficiently.

With the latent fingerprint detection method having the configuration described in the above [vi], it is easy to handle on-site, and the latent fingerprint is detectable clearly.

With the heating evaporation device for detecting a latent fingerprint having the configuration described in the above [vii], the chemical agent can be heated to the high temperatures of 250-450° C. in a short time by the heat generator using the heat of reaction of the hydrolysis exothermic agent that heats by itself upon reaction with water. By allowing the chemical agent to evaporate from the heat generator while being heated at the high temperatures of 350° C. or more, the 2-cyanoacrylic acid ester and the dye are gasified. By heating the chemical agent at the high temperatures of 250° C. or more, besides the 2-cyanoacrylic acid ester, a 2-cyanoacrylic acid ester polymer composed of a monomer alone, a 2-cyanoacrylic acid ester polymer composed of a plurality of kinds of monomers, a mixture of 2-cyanoacrylic acid ester polymers that differ in polymerization degree, a compound containing a 2-cyanoacrylic acid ester incorporating therein an alkyl group and a vinyl group, and a copolymer including a pigment having a higher gasification temperature can be depolymerized, gasified, and evaporated. By exposing the specimen to the atmosphere of the mixed gas of the 2-cyanoacrylic acid ester and the dye, the polymerization of the 2-cyanoacrylic acid ester and the adsorption of the dye occur selectively on the latent fingerprint on the specimen, thereby obtaining a dyed fingerprint image by the one-time processing. The heating evaporation device for detecting a latent fingerprint achieves the high temperatures in the short time, and hence a high-concentration chemical agent gas occurs. This ensures that a clear latent fingerprint is actualized without requiring flames or a power source.

With the heating evaporation device for detecting a latent fingerprint having the configuration as described in the above [viii], it quickly reaches high temperatures in a short time. Therefore, a high-concentration 2-cyanoacrylic acid ester gas, and a high-concentration mixed gas of the 2-cyanoacrylic acid ester and the dye occur, thus allowing a clearer latent fingerprint to be actualized by the one-time processing.

With the latent fingerprint detection apparatus having the configuration described in the above [ix], a clear latent fingerprint is simply detectable anywhere with a lightweight simple structure without using flames and a stationary power source.

With the composition for detecting a latent fingerprint having the configuration described in the above [x], there is no possibility that the 2-cyanoacrylic acid ester generated by heating is repolymerized before reaching a fingerprint, and hence the latent fingerprint is detectable efficiently.

While the present invention has been described in detail with reference to the specific embodiments, it is apparent to those skilled in the art that various changes and modifications are applicable without departing from the spirit and scope of the present invention.

EXAMPLES

<Measurement of Gasification Temperature of Anthraquinone-Based Dye (Sublimation Dye)>

1. Analyzer
   "EXSTAR6000" produced by Seiko Instruments Inc.
2. Measurement Conditions
   Heating temperature: 5° C./min
   Measurement temperature: 40-450° C.
   Atmosphere: Air
3. Measurement Method
   Using the analyzer, 2-phenoxy-1-amino-4-hydroxyanthracene-9,10-dione (product name: Kayaset Red B, produced by Nippon Kayaku Co., Ltd.) was subjected to thermal analysis (TG (thermogravimetry)—DTA (differential thermal distribution)), and a gasification temperature was measured. The result thereof is shown in FIG. 5.

Figure 5:
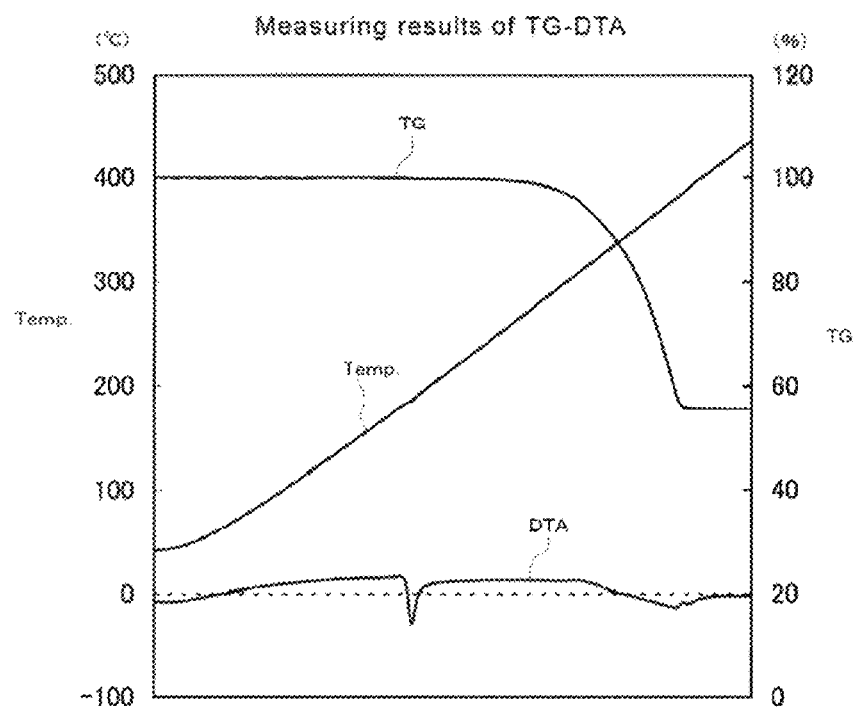
FIG. 5 is a graph showing measuring results of the gasification temperature of an anthraquinone-based dye.

As shown in FIG. 5, it can be seen that the heating temperature of 350° C. or more is required to sufficiently gasify the Kayaset Red B.

<Spectral Curve Measurement of Dye>

1. Analyzer

Microscopic spectrophotometer ("MSP800" produced by J&M)

2. Dye

Anthraquinone-based dye: 2-phenoxy-1-amino-4-hydroxyanthracene-9,10-dione (product name: Kayaset Red B, produced by Nippon Kayaku Co., Ltd.)

3. Measurement Method

An absorption spectrum of the 2-phenoxy-1-amino-4-hydroxyanthracene-9,10-dione was measured using the microscopic spectrophotometer. The result thereof is shown in a spectral distribution curve in FIG. 6.

Figure 6:
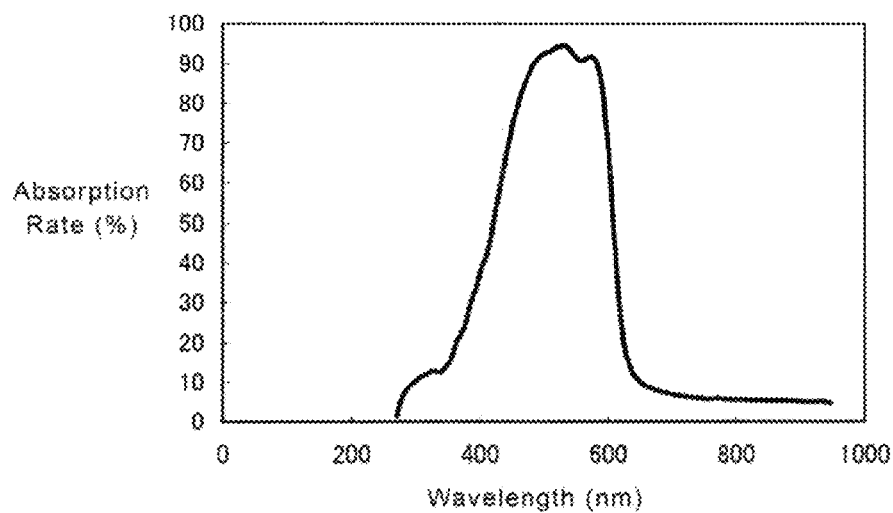
FIG. 6 is a graph showing measuring results of a spectral distribution curve of a fluorescence reagent.

As shown in FIG. 6, it can be seen that the 2-phenoxy-1-amino-4-hydroxyanthracene-9,10-dione has an absorption rate of 50% or more when the wavelength of light is in the range of 450 nm to 600 nm.

<Measurement of Gasification Temperature of Composition for Detecting Latent Fingerprint>

1. Analyzer

"EXSTAR6000" produced by Seiko Instruments Inc.

2. Measurement Conditions

Heating temperature: 5° C./min
Measurement temperature: 0-450° C.
Atmosphere: Air 3. Production of 2-Cyanoacrylic Acid Ester Polymer Methanol containing 1% by mass of water was added to 10 g of ethyl 2-cyanoacrylate. This was allowed to stand at 25° C. for one day or more so as to complete polymerization. After this polymerized matter was dissolved in 300 ml of acetone, the acetone solution was subjected to reprecipitation in three separate parts by using 200 ml of methanol, followed by suction filtration and drying under reduced pressure, thereby obtaining ethyl 2-cyanoacrylate polymer powder.

4. Washing of Dye

A total of 55 parts by mass was obtained by adding 5 parts by mass of the anthraquinone-based dye, namely, the 2-phenoxy-1-amino-4-hydroxyanthracene-9,10-dione (product name: Kayaset Red B, produced by Nippon Kayaku Co., Ltd.) or a naphthalimide-based dye, namely, 2-buthyl-6-(butylamino)-1H-benz[de]isoquinoline-1,3(2H)dione (product name: Kayaset Flavine FG, produced by Nippon Kayaku Co., Ltd.) to 50 parts by mass of 1% methanol solution of methanesulfonic acid. This was mixed and stirred for five minutes, followed by suction filtration and drying under reduced pressure, thereby obtaining a purified dye.

5. Chemical Agent

A) The ethyl 2-cyanoacrylate polymer powder and the anthraquinone-based purified dye were mixed in the ratio of 1:2, thereby obtaining 10 mg of the resulting mixture.

B) The ethyl 2-cyanoacrylate polymer powder and the naphthalimide-based purified dye were mixed in the ratio of 2:3, thereby obtaining 12 mg of the resulting mixture.

6. Measurement Method

Using the analyzer, the anthraquinone-based purified dye and the chemical agent A were respectively subjected to the thermal analysis (TG (thermogravimetry)—DTA (differential thermal distribution)), and their respective gasification temperatures were measured. The results thereof are respectively shown in FIGS. 7(a) and 7(b). Similarly, the naphthalimide-based purified dye and the chemical agent B were respectively subjected to the thermal analysis, and their respective gasification temperatures were measured. The results thereof are respectively shown in FIGS. 8(a) and 3(b).

Figure 7A:
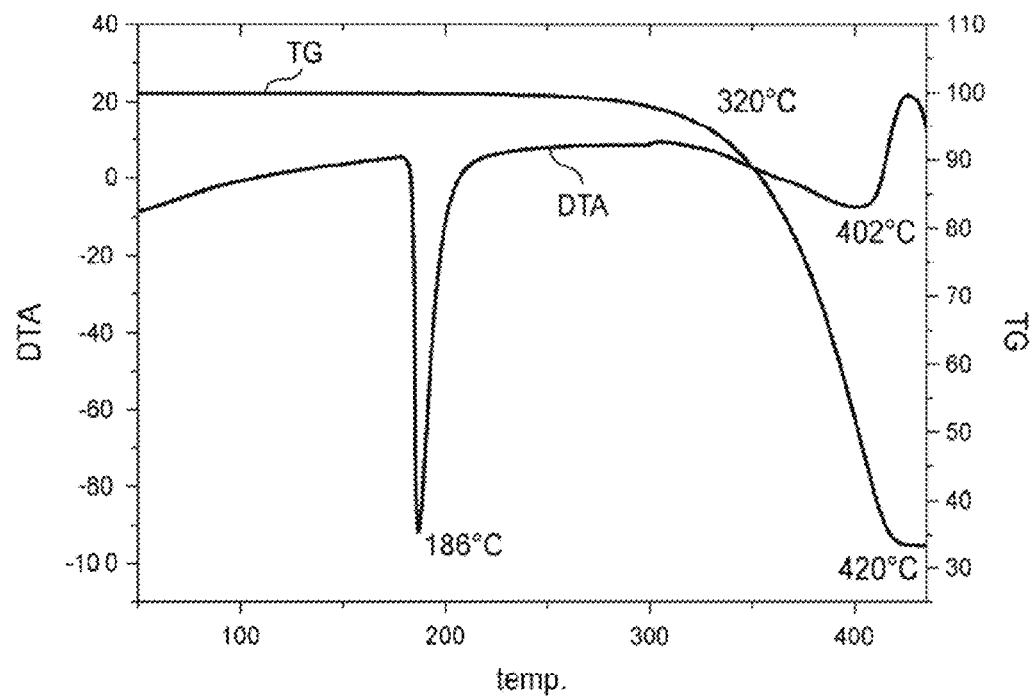
FIG. 7(a) is a graph showing measuring results of the gasification temperature of the anthraquinone-based dye.
Figure 7B:
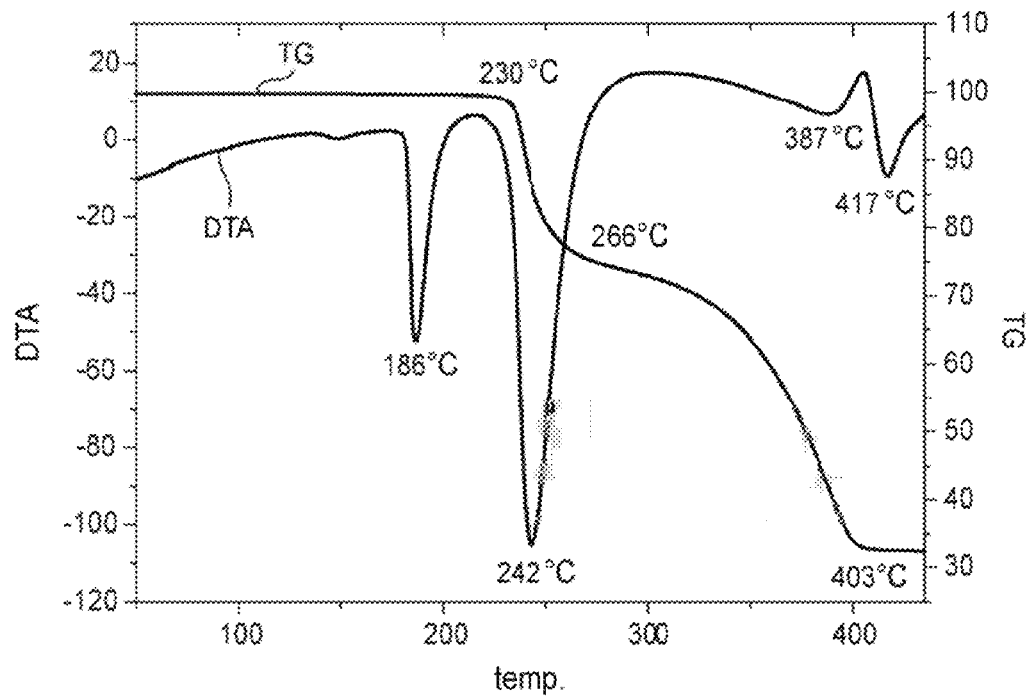
FIG. 7(b) is a graph showing measuring results of the gasification temperature of a mixture of the anthraquinone-based dye and a 2-cyanoacrylic acid ester polymer.

The following matters were found from FIGS. 7(a) and 7(b). That is, with the anthraquinone-based purified dye alone, dissolution occurred at approximately 186° C., gasification (vaporization) started at approximately 320° C., and the gasification was terminated at approximately 420° C. (FIG. 7(a)). With the chemical agent A as the mixture of the ethyl 2-cyanoacrylate polymer powder and the anthraquinone-based purified dye, the anthraquinone-based purified dye was dissolved at approximately 186° C., and the ethyl 2-cyanoacrylate polymer was dissolved at approximately 242° C. Gasification occurred at approximately 230° C. and at approximately 300° C., and the gasification was terminated at approximately 403° C. (FIG. 7b).

Figure 8A:
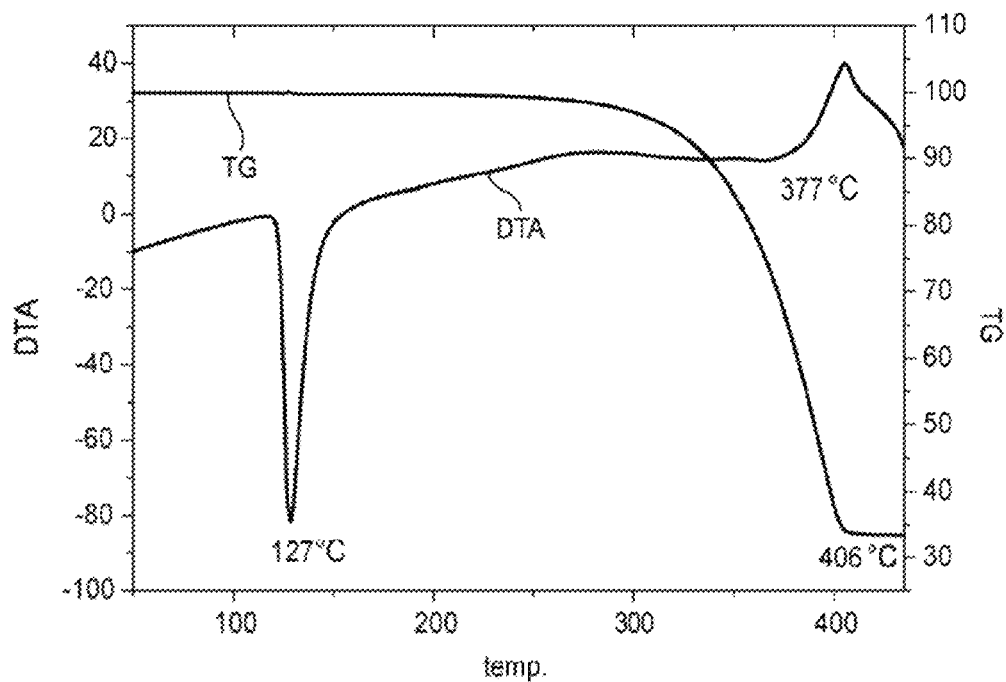
FIG. 8(a) is a graph showing measuring results of the gasification temperature of a naphthalimide-based dye.
Figure 8B:
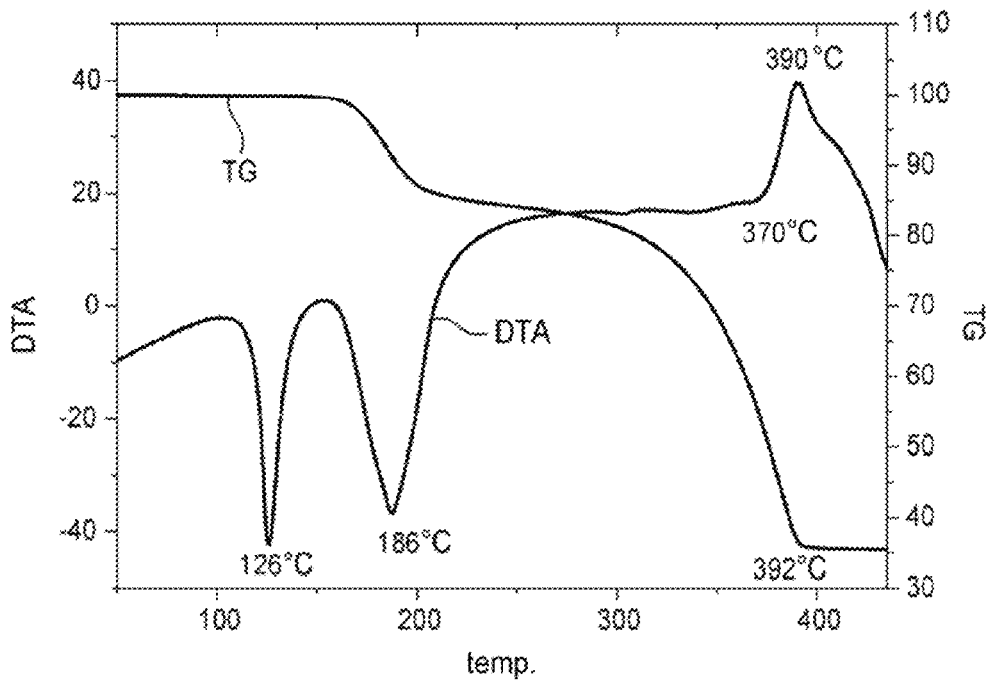
FIG. 8(b) is a graph showing measuring results of the gasification temperature of a mixture of the naphthalimide-based dye and the 2-cyanoacrylic acid ester polymer.

The following matters were found from FIGS. 8(a) and 8(b). That is, with the naphthalimide-based purified dye alone, dissolution occurred at approximately 127° C., gasification started at approximately 320° C., and the gasification was terminated at approximately 406° C. (FIG. 8(a)). With the chemical agent B as the mixture of the ethyl 2-cyanoacrylate polymer powder and the naphthalimide-based purified dye, the naphthalimide-based purified dye was dissolved at approximately 126° C., and the ethyl 2-cyanoacrylate polymer was dissolved at approximately 186° C. Gasification occurred at approximately 180° C. and at approximately 300° C., and the gasification was terminated at approximately 392° C. (FIG. 8b).

From the above, it is clear that the vaporization temperature of the dye is lowered by mixing the ethyl 2-cyanoacrylate polymer powder and the aye.

Fingerprint Detection Test 1

Example 1

(Test Conditions)

1. Latent Fingerprint Detection Apparatus

The latent fingerprint detection apparatus 200 shown in FIG. 3 (the size of the specimen storage part 63: 27 cm in depth×27 cm in width×43 cm in height)

2. Production of 2-Cyanoacrylic Acid Ester Polymer

Methanol containing 1% by mass of water was added to 10 g of ethyl 2-cyanoacrylate. This was allowed to stand at 25° C. for one day or more so as to complete polymerization. After this polymerized matter was dissolved in 300 ml of acetone, the acetone solution was subjected to reprecipitation in three separate parts by using 200 ml of methanol, followed by suction filtration and drying under reduced pressure, thereby obtaining ethyl 2-cyanoacrylatepolymer powder.

3. Washing of Dye

A total of 55 parts by mass was obtained by adding 5 parts by mass of the anthraquinone-based dye "Kayaset Red B" (product name, produced by Nippon Kayaku Co., Ltd.) to 50 parts by mass of 1% methanol solution of methanesulfonic acid. This was mixed and stirred for five minutes, followed by suction filtration and drying under reduced pressure, thereby obtaining a purified dye.

4. Chemical Agent

The ethyl 2-cyanoacrylate polymer powder and the purified dye were mixed in the ratio of 9:1, thereby obtaining 0.7 g of the resulting mixture.

5. Specimen

A commercially available drink can (5 cm in diameter× 10.5 cm in height) was used as a specimen 41, and a fingerprint was attached to a middle part of the drink can. A line was drawn aside of a latent fingerprint so that one can see the position of the latent fingerprint.

6. Test Method

The specimen 41 was mounted inside the specimen storage part 63 in the storage case 81 of the latent fingerprint detection apparatus 200 shown in FIG. 3, and the opening 52 of the side wall 47 was closed by the lid body 56 made of the transparent acrylic plate having a fingerprint attached to the inside of the specimen storage part 63. The 0.7 g of the chemical agent 20 was loaded in the chemical agent storage part 15 of the heating evaporation device 11 for detecting a latent fingerprint, and the metal cylindrical pipe 71 having an inner diameter of 3.45 cm and a length of 6 cm was secured so that the height thereof in the storage case was 3 cm. The heating evaporation device 11 for detecting a latent fingerprint immersed in the water-filled water supply container 39 was disposed in the heating evaporation device mounting space 64 so that the cylindrical pipe 71 secured to the chemical agent storage part 15 passed through the bottom surface opening 50a of the storage case 81. Calcium oxide (quicklime) was used as the hydrolysis exothermic agent 21.

After one minute from the start of gasification of the chemical agent 20, it was confirmed that the fuming from the heating evaporation device 11 for detecting a latent fingerprint was settled. The specimen 41 was exposed to the gasified chemical agent 20 in the storage case 81 for one hour.

After the elapse of the one hour, it was confirmed that the ethyl 2-cyanoacrylate polymer was sufficiently attached to the latent fingerprint attached to the inside of the lid body 56 secured to the opening 52 of the storage case 81. Thereafter, the specimen 41 was unloaded from the storage case 81.

Figure 9D:
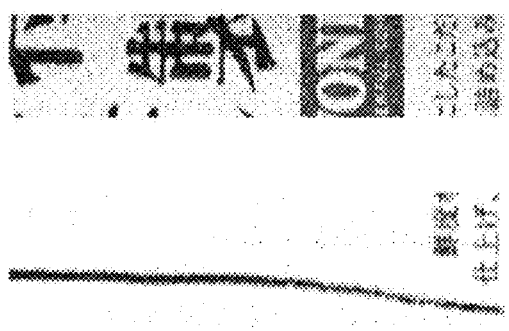
FIGS. 9(a) to 9(d) are images of fluorescent fingerprints obtained in Example 1.
Figure 9C:
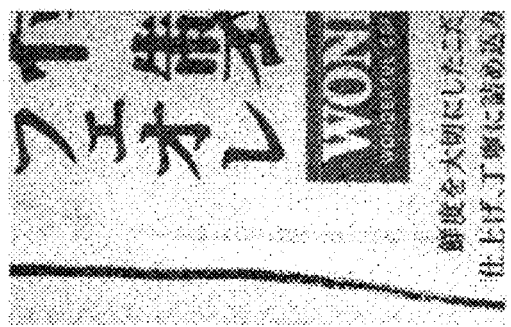
Figure 9B:
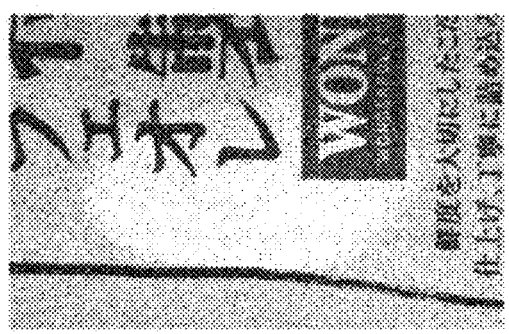
Figure 9A:
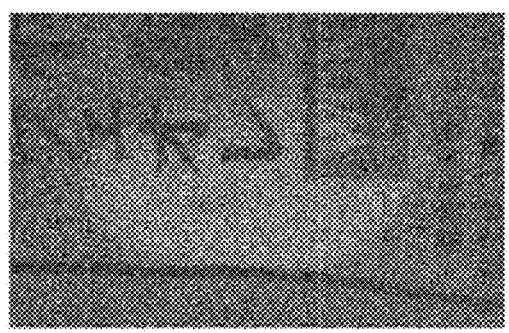

Lights of 415 nm to 575 nm were irradiated using a CRIMESCOPE (model number: CS-16-500 (produced by HORIBA Scientific) to the detected fingerprint thus obtained, and fluorescent fingerprint images were observed using a filter for cutting the irradiation light. The observation results are presented in Table 1. The observed fluorescent fingerprints were photographed using a digital camera. The observed images are shown in FIGS. 9(a) to 9(d). FIG. 9(a) is an image when observed by irradiation of visible light, FIG. 9(b) is an image when observed by irradiation of light having a wavelength of 415 nm, FIG. 9(c) is an image when observed by irradiation of light having a wavelength of 495 nm, and FIG. 9(d) is an image when observed by irradiation of light having a wavelength of 575 nm.

As a simple method, a blue LED (465 nm) or a blue-green LED (495 nm) was irradiated, and fluorescent fingerprint images were observed through an orange goggle or a red goggle as a filter. The observation results are presented in Table 2.

The degrees of fluorescent fingerprint detections in Tables 1 and 2 were evaluated as follows.

Symbol "○" denotes that continuous fluorescent fingerprint ridges can be observed clearly.

Symbol "x" denotes that the fluorescent fingerprint ridges cannot be observed or are difficult to observe.

Furthermore, almost no chemical agent 20 remained in the chemical agent storage part 15 of the heating evaporation device 11 for detecting a latent fingerprint after the test was terminated. It was found that the chemical agent 20 was completely gasified and evaporated in a short time by using the heating evaporation device 11 for detecting a latent fingerprint of the present invention.

Comparative Example 1

A fingerprint detection test was conducted similarly to Example 1, except that the dye in Example 1 was replaced with p-dimethylaminobenzaldehyde.

The lights of 415 nm to 575 nm were irradiated using the CRIMESCOPE to the detected fingerprint thus obtained, and fluorescent fingerprint images were observed using the filter for cutting the irradiation lights. Further, the blue LED (465 nm) or the blue-green LED (495 nm) was irradiated to observe a fluorescent fingerprint image through the orange goggle or the red goggle as a filter. The results are presented in Tables 1 and 2.

Comparative Example 2

(Test Conditions)

1. Latent Fingerprint Detection Apparatus

Figure 4:
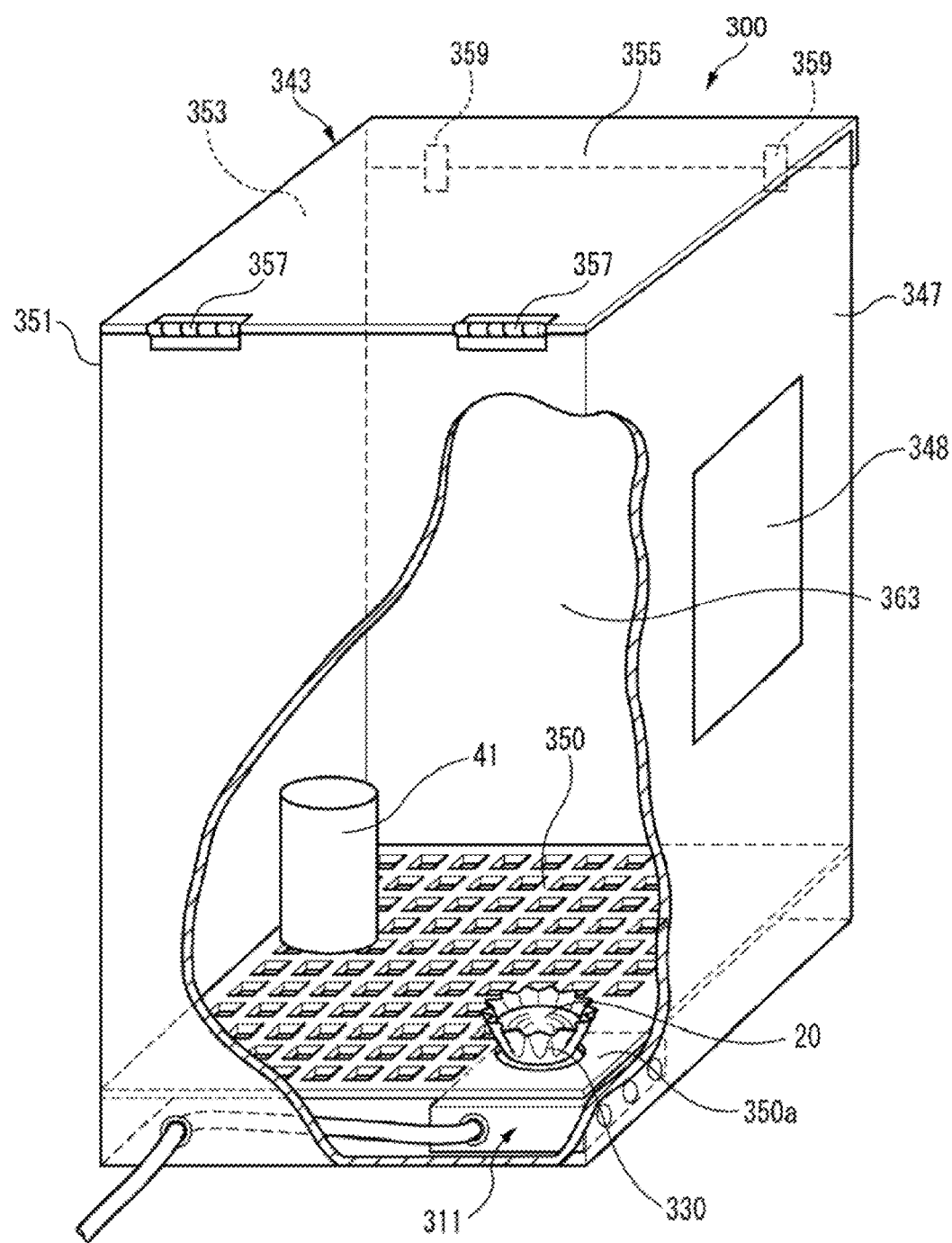
FIG. 4 is a partially cut-away perspective view showing a conventional latent fingerprint detection apparatus.

The latent fingerprint detection, apparatus 300 shown in FIG. 4 (product name: FUMING BOX, produced by POLICE SCIENCE INDUSTRY, LTD., and the size of the specimen storage part 363: 27 cm in depth×27 cm in width×43 cm in height)

The latent fingerprint detection apparatus 300 included a heating device 311 using a heater, and a storage case 343 to store a specimen 41 therein. A chemical agent 20 gasified by the heating device 311 was allowed to fill the storage case 343.

The storage case 343 was a box having a rectangular parallelepiped shape, and included a body 351 made up of a side wall 347 and a bottom wall 349, and a lid body 355 that served as a top plate and closed an upper opening 353 of the body 351. The heating device 311 was put on a lower part of the specimen storage part 363 partitioned by a metal mesh rack 350 having a large number of holes.

The lid body 355 of the storage case 343 included a flat plate part having approximately the same shape as the upper opening 353 of the body 351, a hinge 357 connected to the upper opening 353 so as to permit rotation of one side of the flat plate part, and a hook 359 that was disposed on the side wall 347 on the opposite side of the hinge 357 and locked an opening-closing end of the lid body 355. The side wall 347 of the storage case 343 included a transparent window 348 that permitted observation of the interior of the storage case 343. The storage case 343 thus configured had predetermined air tightness under the condition that the lid body 355 closing the upper opening 353 was rocked by the hook 359. The specimen storage part 363 was located above the mesh rack 350 in the interior of the storage case 343, and the specimen 41 was stored in the specimen storage part 363.

2. Chemical Agent

The ethyl 2-cyanoacrylate polymer powder and the purified dye which were produced in Example 1 were mixed in the ratio of 9:1, thereby obtaining 0.7 g of the resulting mixture.

3. Specimen

A commercially available drink can (5 cm in diameter× 10.5 cm in height) was used as a specimen 41, and a fingerprint was attached to a middle part of the drink can.

4. Test Method

A heating switch of the latent fingerprint detection apparatus 300 shown in FIG. 4 was turned on. After the elapse of approximately 10 minutes, it was confirmed that a temperature indication of the heating device reached a maximum temperature of 230° C. After confirming the temperature indication of 230° C., the lid body 355 of the storage case 343 was opened to put the specimen 41 on the mesh rack 350 in the storage case 343 of the latent fingerprint detection apparatus 300, and an aluminum cup 330 holding the 0.7 g of the chemical agent 20 was mounted on a chemical agent mounting part 350a on the heating device 311. A fingerprint was attached to the inside of the transparent window 348, and the upper opening 353 was closed by the lid body 355 and was locked to the side wall 347 by the hook 359.

The chemical agent 20 was heated by the latent fingerprint detection apparatus 300 for 10 minutes so as to be heated and evaporated. The specimen 41 was further exposed to the chemical agent 20 in the storage case 343 for one hour.

After the elapse of the one hour, it was confirmed that the cyanoacrylate polymer was sufficiently attached to the latent fingerprint attached to the transparent window 348 of the latent fingerprint detection apparatus 300. Thereafter, the specimen 41 was unloaded from the storage case 343.

Lights of 415 nm to 575 nm were irradiated using the CRIMESCOPE to the detected fingerprint thus obtained, and fluorescent fingerprint images were observed using the filter for cutting the irradiation lights. The observation results are presented in Table 1. The observed fluorescent fingerprints were photographed using the digital camera. The observed images are shown in FIGS. 10(a) to 10(d). FIG. 10(a) is an image when observed by irradiation of visible light, FIG. 10(b) is an image when observed by irradiation of light having the wavelength of 415 nm, FIG. 10(c) is an image when observed by irradiation of light having the wavelength of 495 nm, and FIG. 10(d) is an image when observed by irradiation of light having the wavelength of 575 nm.

As a simple method, the blue LED (465 nm) or the blue-green LED (495 nm) was irradiated to observe whether a fluorescent fingerprint image was visible through the orange goggle or the red goggle as a filter. The observation results are presented in Table 2.

The dye (anthraquinone-based dye) was partially dissolved in the aluminum cup 330 after the test was terminated, but the dye mostly remained, failing to sufficiently gasify the chemical agent 20.

TABLE 1

Results detected by a CRIMESCOPE

|  | Visible light | Excitation wavelength of 415 nm | Excitation wavelength of 495 nm | Excitation wavelength of 575 nm |
|---|---|---|---|---|
| Example 1 | ※1 | ○ | ○ | ○ |
| Comparative Example 1 | ※2 | x | x | x |
| Comparative Example 2 | x | x | x | x |

※1: Under visible light, fingerprint ridges could be visually observed as fingerprints of white ethyl 2-cyanoacrylate polymer which are not fluorescent and are slightly reddish.
※2: Under visible light, fingerprint ridges could be visually observed as fingerprints of white ethyl 2-cyanoacrylate polymer which are not fluorescent.

TABLE 2

Results detected by an LED light

|  | Blue LED (465 nm) | | Blue LED (495 nm) | |
|---|---|---|---|---|
|  | Orange goggle | Red goggle | Orange goggle | Red goggle |
| Example 1 | ○ | ○ | ○ | ○ |
| Comparative Example 1 | x | x | x | x |
| Comparative Example 2 | x | x | x | x |

The present inventors observed the fluorescent fingerprint of Example 1 through the orange goggle or the red goggle, and they were capable of clearly observing continuous fluorescent fingerprint ridges when using either the blue LED or the blue-green LED.

As apparent from the observation results in Tables 1 and 2, as well as the results in FIGS. 9(a) to 9(d) and FIGS. 10(a) to 10(d), it was confirmed that Example 1 was capable of defecting the clear latent fingerprint. It was also found that the dye having a wide excitation range could be gasified concurrently with the gasification of the 2-cyanoacrylic acid ester. This ensured the fluorescent fingerprint detections in a wide wavelength, as well as the detections using a portable simple LED light.

Fingerprint Detection Test 2

Example 2

(Test Conditions)
1. Latent Fingerprint Detection Apparatus
   The latent fingerprint detection apparatus 200 shown in FIG. 3 (the size of the specimen storage part 63: 27 cm in depth×27 cm in width×43 cm in height)
2. Production of 2-Cyanoacrylic Acid Ester Polymer
   Methanol containing 1% by mass of water was added to 10 g of ethyl 2-cyanoacrylate. This was allowed to stand at 25° C. for one day or more so as to complete polymerization. After this polymerized matter was dissolved in 300 ml of acetone, the acetone solution was subjected to reprecipitation in three separate parts by using 200 ml of methanol, followed by suction filtration and drying under reduced pressure, thereby obtaining ethyl 2-cyanoacrylatepolymer powder.
3. Dye
   A total of 55 parts by mass was obtained by adding 5 parts by mass of the anthraquinone-based dye "Kayaset Red B" (product name, produced by Nippon Kayaku Co., Ltd.) to 50 parts by mass of 1% methanol solution of methanesulfonic acid. This was mixed and stirred for five minutes, followed by suction filtration and drying under reduced pressure, thereby obtaining a purified dye.
4. Chemical Agent
   The ethyl 2-cyanoacrylate polymer powder and the purified dye were mixed in the ratio of 2:1, thereby obtaining 70 mg of the resulting mixture.
5. Specimen
   A commercially available drink can (5 cm in diameter× 10.5 cm in height) was used as a specimen 41, and a fingerprint was attached to a middle part of the drink can.
6. Test Method
   The fingerprint was detected with a similar method to that of Example 1.
   Lights of 415 nm to 575 nm were irradiated using the CRIMESCOPE to the detected fingerprint thus obtained, and fluorescent fingerprint images were observed using the filter for cutting the irradiation lights. The observation results are presented in Table 3. The observed fluorescent fingerprints were photographed using the digital camera. The observed images are shown in FIGS. 11(a) to 11(e). FIG. 11(a) is an image when observed by irradiation of visible light, FIG. 11(b) is an image when observed by irradiation of light having a wavelength of 415 nm, FIG. 11(c) is an image when observed by irradiation of light having a wavelength of 455 nm. FIG. 11(a) is an image when observed by irradiation of light having a wavelength of 495 nm, and FIG. 11(e) is an image when observed by irradiation of light having a wavelength of 575 nm.

Example 3

1. Dye

A total of 55 parts by mass was obtained by adding 5 parts by mass of the naphthalimide-based dye "Kayaset Flavine FG" (product name, produced by Nippon Kayaku Co., Ltd.) to 50 parts by mass of 1% methanol solution of methanesulfonic acid. This was mixed and stirred for five minutes, followed by suction filtration and drying under reduced pressure, thereby obtaining a purified dye.

2. Chemical Agent

The ethyl 2-cyanoacrylate polymer powder produced in Example 2 and the purified dye were mixed in the ratio of 1:2, thereby obtaining 70 mg of the resulting mixture.

3. Specimen

A commercially available drink can (5 cm in diameter× 10.5 cm in height) was used as a specimen 41, and a fingerprint was attached to a middle part of the drink can.

6. Test Method

The fingerprint was detected with a similar method to that of Example 1.

Lights of 415 nm to 495 nm were irradiated using the CRIMESCOPE to the detected fingerprint thus obtained, and fluorescent fingerprint images were observed using the filter for cutting the irradiation lights. The observation results are presented in Table 3. The observed fluorescent fingerprints were photographed using the digital camera. The observed images are shown in FIGS. 12(a) to 12(d). FIG. 12(a) is an image when observed by irradiation of visible light, FIG. 12(b) is an image when observed by irradiation of light having a wavelength of 415 nm, FIG. 12(c) is an image when observed by irradiation of light having a wavelength of 455 nm, and FIG. 12(d) is an image when observed by irradiation of light having a wavelength of 495 nm.

TABLE 3

Results detected by a CRIMESCOPE

| | Visible light | Excitation wavelength of 415 nm | Excitation wavelength of 455 nm | Excitation wavelength of 495 nm | Excitation wavelength of 575 nm |
|---|---|---|---|---|---|
| Example 2 | ※1 | ○ | ○ | ○ | ○ |
| Example 3 | ※3 | ○ | ○ | ○ | |

※1: Under visible light, fingerprint ridges could be visually observed as fingerprints of white ethyl 2-cyanoacrylate polymer which are not fluorescent and are slightly reddish.
※3: Under visible light, fingerprint ridges could be visually observed as fingerprints of white ethyl 2-cyanoacrylate polymer which are not fluorescent and are slightly yellowish.

As apparent from the observation results in Table 3, as well as the results in FIGS. 11(a) to 11(d) and FIGS. 12(a) to 12(e), it was confirmed that Examples 2 and 3 were capable of detecting the clear latent fingerprint. It was also found that the dye having a wide excitation range could be gasified concurrently with the gasification of the 2-cyanoacrylic acid ester. This ensured the fluorescent fingerprint detections in a wide wavelength.

Fingerprint Detection Test 3

Example 4

1. Dye

A total of 55 parts by mass was obtained by adding 5 parts by mass of the anthraquinone-based dye "Kayaset Red B" (product name, produced by Nippon Kayaku Co., Ltd.) to 50 parts by mass of 1% methanol solution of me thane sulfonic acid. This was mixed and stirred for five minutes, followed by suction filtration and drying under reduced pressure, thereby obtaining a purified dye.

2. Chemical Agent

The ethyl 2-cyanoacrylate polymer powder produced in Example 2 and the purified dye were mixed in the ratio of 1:2, thereby obtaining 70 mg of the resulting mixture.

3. Specimen

An aluminum tape was used as a specimen 41, and a fingerprint was attached to a luster part of the tape. The specimen 41 was put in a plastic bag with a zipper, and was preserved in a dark chamber (a desk drawer) at room temperature for three months so as to obtain an old fingerprint. As a control, a fingerprint was attached to the luster part of the specimen 41 three hours before starting the test, thereby obtaining a new fingerprint.

4. Test Method

The fingerprint was detected with a similar method to that of Example 1.

Figure 13A:
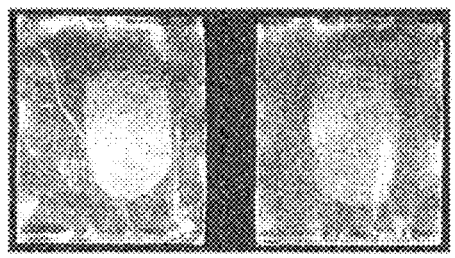
FIGS. 13(a) to 13(e) are images of fluorescent fingerprints obtained in Example 4.
Figure 13B:
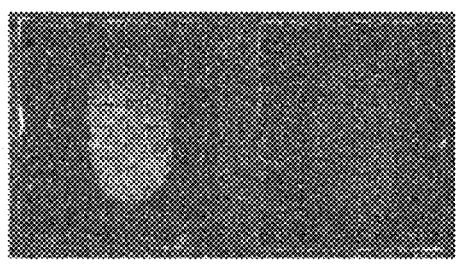
Figure 13C:
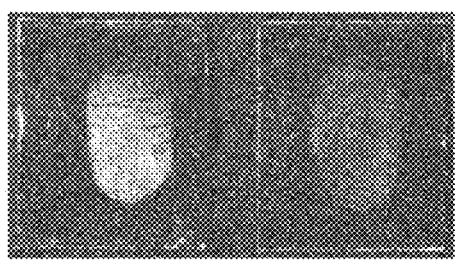
Figure 13D:
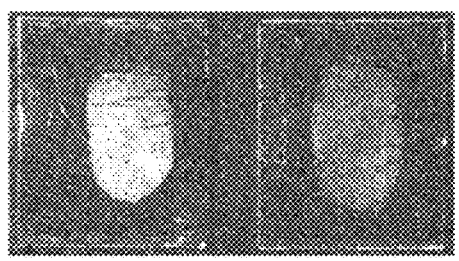
Figure 13E:
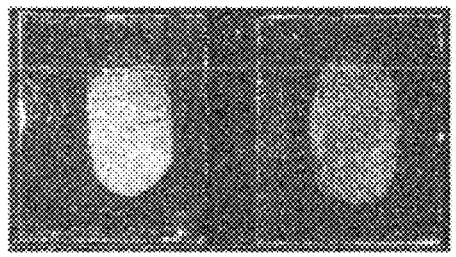

Lights of 415 nm to 575 nm were irradiated using the CRIMESCOPE to the detected fingerprints thus obtained, and fluorescent fingerprint images were observed using the filter for cutting the irradiation lights. The observed fluorescent fingerprints were photographed using the digital camera. The observed images are shown in FIGS. 13(a) to 13(e), FIG. 13(a) show images when observed by irradiation of visible light, FIG. 13(b) shows images when observed by irradiation of light having a wavelength of 415 nm, FIG. 13(c) shows images when observed by irradiation of light having a wavelength of 455 nm, FIG. 13(d) shows images when observed by irradiation of light having a wavelength of 495 nm, and FIG. 13(e) shows images when observed by irradiation of light having a wavelength of 575 nm. In each of these drawings, the fingerprint image located leftward corresponds to the new fingerprint, and the fingerprint image located rightward corresponds to the old fingerprint.

As apparent from the results in FIGS. 13(a) to 13(e), it was found that Example 4 was capable of detecting the clear fingerprint even on the old fingerprint after hours had passed, and was capable of detecting the fluorescent fingerprints in a wide wavelength.

Fingerprint Reducibility Test

Example 5

1. Dye

A total of 55 parts by mass was obtained by adding 5 parts by mass of the anthraquinone-based aye "Kayaset Red B" (product name, produced by Nippon Kayaku Co., Ltd.) to 50 parts by mass of 1% methanol solution of methanesulfonic acid. This was mixed and stirred for five minutes, followed by suction filtration and drying under reduced pressure, thereby obtaining a purified dye.

2. Chemical Agent

The ethyl 2-cyanoacrylate polymer powder produced in Example 2 and the dye were mixed in the ratio of 1:2, thereby obtaining 70 mg of the resulting mixture.

3. Specimen

A commercially available drink can (5 cm in diameter× 10.5 cm in height) was used as a specimen 41, and a fingerprint was attached to a middle part of the drink can.

4. Test Method

The fingerprint was detected with a similar method to that of Example 1.

Subsequently, the detected fingerprint thus obtained was wiped out with a dry tissue paper so as to leave a part of the detected fingerprint (approximately one third on the lower end side thereof), and the ethyl 2-cyanoacrylate polymer and the dye which were attached to the fingerprint were removed.

Figure 14A:
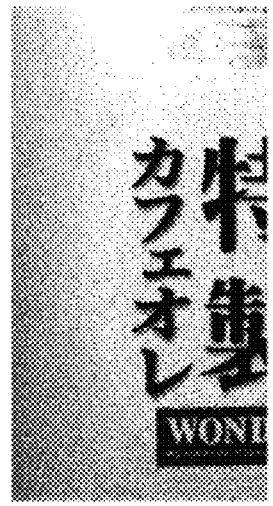
FIGS. 14(a) and 14(b) are images of fluorescent fingerprints obtained in Example 5.
Figure 14B:
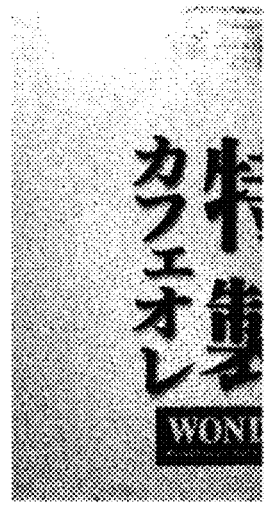

Thereafter, light of 495 nm was irradiated using the CRIMESCOPE, and a fluorescent fingerprint image was observed using the filter for cutting the irradiation light. The observed fluorescent fingerprint was photographed using the digital camera. FIG. 14(a) shows the observed image. FIG. 14(b) shows, as a control, one whose photograph was taken by irradiating the light of 405 nm before wiping out the fingerprint.

Example 6

A similar test to that of Example 5 was conducted except that the dye in Example 5 was replaced with the naphthalimide-based dye "Kayaset Flavine FG" (product name, produced by Nippon Kayaku Co., Ltd.), and the light having a wavelength of 455 nm was irradiated.

Figure 15A:
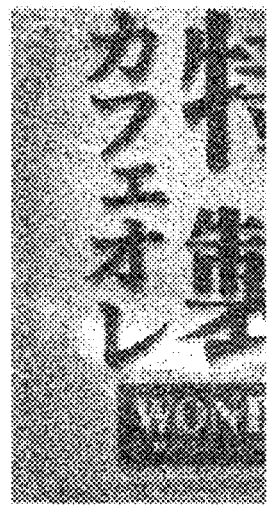
FIGS. 15(a) and 15(b) are images of fluorescent fingerprints obtained in Example 6.
Figure 15B:

FIG. 15(a) shows the observed image that was taken using the digital camera. FIG. 15(b) shows, as a control, one whose photograph was taken by irradiating the light of 455 nm before wiping out the fingerprint.

As apparent from the results in FIGS. 14(a) and 14(b) and FIGS. 15(a) and 15(b), it was found that in Examples 5 and 6, the amount of the ethyl 2-cyanoacrylate polymer to be attached to the fingerprint was small, and hence was easily removable by wiping out, thus having excellent reducibility.

While the present invention has been described in detail with reference to the specific embodiments, it is apparent to those skilled in the art that various changes and modifications are applicable without departing from the spirit and scope of the present invention. The present invention is based on Japanese Patent Applications (Nos. 2012-235678 and 2012-236004) filed Oct. 25, 2012, the contents of which are incorporated herein by reference.

INDUSTRIAL APPLICABILITY

With the heating evaporation device for detecting a latent fingerprint, the latent fingerprint detection apparatus, and the latent fingerprint detection method according to the present invention, a clearer latent fingerprint is detectable anywhere by heating the chemical agent at high temperatures in a short time without using flames or a power source.

DESCRIPTION OF THE REFERENCE NUMERAL 11 heating evaporation device for detecting latent fingerprint
13 outer container
14 partition member
15 chemical agent storage part
17 heat generator
19 lid member
20 chemical agent
21 hydrolysis exothermic agent
22 hot-melt film
23 water passage hole
27 unwoven sheet
39 water supply container
41 specimen
43, 81 storage case
45 top plate
47 side wall
43 transparent window
49, 50 bottom wall
51 body
59 hook
63 specimen storage part
64 heating evaporation device mounting space
67 leg part
100, 200 latent fingerprint detection apparatus

The invention claimed is:

1. A latent fingerprint detection method comprising:
a heating step of heating to 250° C. to 450° C. a chemical agent to be gasified by heating so as to attach to a latent fingerprint on a specimen; and
an exposure step of exposing the specimen having the latent fingerprint attached thereto to an atmosphere of the gasified chemical agent, wherein the chemical agent is a mixture of a 2-cyanoacrylic acid ester polymer and a dye, which is an anthraquinone-based dye or naphthalimide-based dye, and wherein the method includes a light irradiation step of irradiating visible light to a fingerprint raised on the surface of the specimen.

2. The latent fingerprint detection method according to claim 1, wherein the anthraquinone based dye is at least one selected from the group consisting of amino anthraquinone, aminohydroxy anthraquinone diamino anthraquinone, dihydroxy anthraquinone, and diaminodihydroxy anthraquinone, and the naphthalimide-based dye is at least one selected from the group consisting of alkyl naphthalimide, alkoxy naphthalimide, alkoxyalkyl naphthalimide, amino naphthalimide, alkylamino naphthalimide, nitro naphthalimide, halogenated naphthalimide, carbonyl naphthalimide, phenylthio naphthalimide cyano naphthalimide, and hydroxy naphthalimide.

3. The latent fingerprint detection method according to claim 1, wherein the 2-cyanoacrylic acid ester polymer is obtained by polymerizing alkyl 2-cyanoacrylate having an alkyl group with a carbon number of 1 to 4.

4. The latent fingerprint detection method according to claim 1, wherein the 2-cyanoacrylic acid ester polymer is polymerized using a water-containing alcohol.

5. The latent fingerprint detection method according to claim 1, wherein the heating step comprises heating using a heating evaporation device for detecting a latent fingerprint which includes the chemical agent, a chemical agent storage part to store the chemical agent therein, and a heat generator including the chemical agent storage part to store a hydrolysis exothermic agent therein.

6. The latent fingerprint detection method according to claim 1, wherein the chemical agent is heated to 350° C. to 450° C. in one minute after starting heating.

7. The latent fingerprint detection method according to claim 6, wherein the chemical agent is heated by a hydrolysis exothermic agent.

\* \* \* \* \*